(12) United States Patent
Wardman et al.

(10) Patent No.: US 6,890,948 B1
(45) Date of Patent: May 10, 2005

(54) USE OF INDOLE-3-ACETIC ACID DERIVATIVES IN MEDICINE

(75) Inventors: Peter Wardman, Northwood (GB); Lisa Folkes, Northwood (GB); Gabriele U. Dachs, Northwood (GB); Sharon Rossiter, Northwood (GB); Olga Greco, Northwood (GB)

(73) Assignee: Cancer Research Technology Limited, London (GB)

( * ) Notice: Subject to any disclaimer, the term of this patent is extended or adjusted under 35 U.S.C. 154(b) by 17 days.

(21) Appl. No.: 10/311,332

(22) PCT Filed: Jun. 28, 2001

(86) PCT No.: PCT/GB01/02872

§ 371 (c)(1),
(2), (4) Date: Apr. 8, 2003

(87) PCT Pub. No.: WO02/02110

PCT Pub. Date: Jan. 10, 2002

(30) Foreign Application Priority Data

Jun. 30, 2000 (GB) .............................. 0016162

(51) Int. Cl.[7] .............................................. A61K 31/40
(52) U.S. Cl. ..................................................... 514/419
(58) Field of Search ................................ 514/418, 419

(56) References Cited

U.S. PATENT DOCUMENTS

| | | | | |
|---|---|---|---|---|
| 3,689,657 A | * | 9/1972 | Share et al. ................. | 514/382 |
| 3,901,914 A | * | 8/1975 | Hannah ....................... | 548/412 |
| 5,684,034 A | * | 11/1997 | Bach et al. .................. | 514/419 |
| 6,017,945 A | * | 1/2000 | Rawson et al. ............. | 514/414 |

FOREIGN PATENT DOCUMENTS

| | | | | |
|---|---|---|---|---|
| WO | WO 88/07378 | | 10/1988 | |
| WO | 94/14434 | * | 7/1994 | 514/419 |

OTHER PUBLICATIONS

Wardman, P., "Indol-3-Acetic Acids and Horseradish Peroxidase: A New Prodrug/Enzyme Combination for Targeted Cancer Therapy," *Current Pharmaceutical Design*, 2002, vol. 8, No. 15, pp. 1363–1374.

Rossiter, S., "A Convenient Synthesis of 3-Methyleneoxindoles: Cytoxic Metabolites of Indole-3-Acetic Acids," *Tetrahedron Letters*, 43, 2002, pp. 4671–4673.

Folkes, L., et al., "Reactivity Toward Thiols and Cytotoxicity of 3-Methylene-2-Oxindoles, Cytotoxins from Indole-3-Acetic Acids, on Activation by Peroxidases," *Chem. Res. Toxicol.*, 2002, vol. 15, No. 6, pp. 887–882.

Rossiter, S., et al., "Halogenated Indole-3-Acetic Acids as Oxidatively Activated Prodrugs with Potential for Targeted Cancer Therapy," *Bioorganic & Medicinal Chemistry Letters 12*, 2002, pp. 2523–2526.

Greco, O., et al., "Horseradish Peroxidase–Mediated Gene Therapy: Choice of Prodrugs in Oxic and Anoxic Tumor Conditions," *Molecular Cancer Therapeutics*, vol. 1, Dec. 2001, pp. 151–160.

Folkes, L., et al., "5-Fluoroindole-3-Acetic Acid: A Prodrug Activated by a Peroxidase with Potential for Use in Targeted Cancer Therapy," *Biochemical Pharmacology*, 63, 2002, pp. 265–272.

Greco, O., et al., "Development of a Novel Enzyme/Prodrug Combination for Gene Therapy of Cancer: *Horseradish Peroxidase/Indole-3-Acetic Acid,*" *Cancer Gene Therapy*, vol. 7, No. 11, 2000, pp. 1414–1420.

Folkes, L., et al., "Oxidative Activation of Indole-3-Acetic Acids to Cytotoxic Species–A Potential New Role for Plant Auxins in Cancer Therapy," *Biochemical Pharmacology*, 61, 2001, pp. 129–136.

Connolly, C., et al., "Transport into and Out of the Golgi Complex Studied by Transfecting Cells with cDNAs Encoding Horseradish Peroxidase," *The Journal of Cell Biology*, vol. 127, No. 3, Nov. 1994, pp. 641–652.

Ben–Yoseph, O., et al., "Oxidation Therapy: The use of a Reactive Oxygen Species–Generating Enzyme System for Tumour Treatment," *Br. J. Cancer*, 1994, vol. 70, pp. 1131–1135.

Edwards, A., et al., "Apoptosis Induction in Nonirradiated Human HL–60 and Murine NSO/2 Tumor Cells by Photoproducts of Indole-3-Acetic Acid and Riboflavin," *Photochemistry and Photobiology*, 1999, 70(4), pp. 645–649.

(Continued)

*Primary Examiner*—Raymond J. Henley, III
(74) *Attorney, Agent, or Firm*—Foley & Lardner LLP

(57) ABSTRACT

Compounds of formula (I), or physiologically functional derivatives thereof, wherein: $R_1$, $R_2$, $R_3$ and $R'_3$ are independently selected from H or lower alkyl; and $R_4$, $R_5$, $R_6$ and $R_7$ are independently selected from H, electron withdrawing groups (such as F, Cl, Br, I, $OCF_3$, carboxyl groups, acetal groups, electron deficient aryl groups), lower alkyl groups lower alkoxy groups, aryl groups or aryloxy groups, wherein it least one of $R_4$, $R_5$, $R_6$, and $R_7$ is selected from an electron withdrawing group, may be used in methods of therapy, particular in treating neoplastic diseases in methods of GDEPT, ADPET, PDEPT and PDT

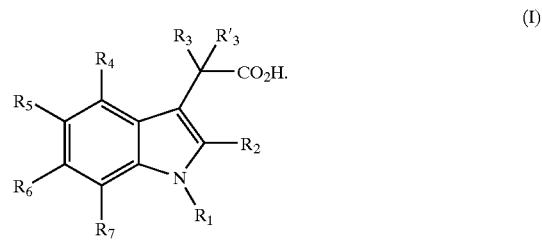

(I)

14 Claims, 9 Drawing Sheets

OTHER PUBLICATIONS

Laliberte, M., et al., "Sulface Modification of Horseradish Peroxidase with Poly(Ethylene Glycol)s of Various Relative Molecular Masses ($M_r$): Relationship between the $M_r$ of Poly(Ethylene Glycol) and the Stability of Horseradish Peroxidase–Poly(Ethylene Glycol) Adducts under Various Denaturing Conditions," *Biotechnol. Appl. Biochem.* 20, 1994, pp. 397–413.

Hart, S., et al., "Lipid–Mediated Enhancement of Transfection by a Nonviral Integrin–Targeting Vector," *Human Gene Therapy*, 9, Mar. 1, 1998, pp. 575–585.

Fortier, G., et al., Surface Modification of Horseradish Peroxidase with Poly(Ethylene Glycol)s of Various Molecular Masses. *Biotechnol. Appl. Biochem.*, 17, 1993, pp. 115–130, Great Britain.

Erdtman, H., et al., "Synthetic Plant Hormones," *Acta Chemica Scandinavica*, 8, 1954, No. 1, pp. 119–123.

Katz, A., et al., "Synthesis and Analgesic Activity of Pemedolac (cis–1–Ethyl–1,3,4, 9–Tetrahydro–4–(Phenylmethyl)Pyrano[3,4–b] indole–1–Actic Acid," *Journal of Medicinic Chemistry*, 31, 1988, pp. 1244–1250.

Carrera, Jr., G., et al., "Synthesis of 6– and 7–Arylinodoles via Palladium–Catalyzed Cross–Coupling of 6–and 7–Bromoindole with Arylboronic Acids," *Synlett.* Jan. 1994, pp. 93–94.

Dillard, R., et al.,"Indole Inhibitors of Human Nonpancreatic Secretory Phospholipase $A_2$_1 Indole–3–Acetamides," *J. Med. Chem.*, 39, 1996, pp. 5119–5136.

Fox, S., et al., "Synthesis of Indole–3–Acetic Acids and 2–Carboxyindole–3–Acetic Acids with Substituents in the Benzene Ring," *J. Am. Chem. Soc.*, vol. 73, Jun. 1951, pp. 2756–2759.

Engvild, K., "Preparation of Chlorinated 3–Indolylacetic Acids," *Acta Chem. Scan. B.*, 31, No. 4, 1977, pp. 338–339.

Vasey, P., et al., "Phase I Clinical and Pharmacokinetic Study of PK1 [N–(2–Hydroxypropyl)Methacrylamide Copolymer Doxorubicin]: First Member of a New Class of Chemotherapeutic Agents–Drug–Polymer Conjugates," *Clinical Cancer Research*, vol. 5, Jan. 1999, pp. 83–94.

Duncan, R., et al., "The Role of Polymer Conjugates in the Diagnosis and Treatment of Cancer," *S.T.P. Pharma Sciences*, 6 (4), 1996, pp. 237–263.

Samoszuk, M., et al.,"Targeting of Glucose Oxidase to Murine Lymphoma Allografts," *Tumor Targeting*, 1, 1995, pp. 37–43.

Bartoli, G., et al., "The Reaction of Vinyl Grignard Reagents with 2–Substituted Nitroarenes: A New Approach to the Synthesis of 7–Substituted Indoles," *Tetrahedron Letters*, vol. 30, No. 16, 1989, pp. 2129–2132, Great Britain.

Bagshawe, K., et al., "Antibody–Enzyme Conjugates Can Generate Cytotoxic Drugs from Inactive Precursors at Tumor Sites," *Antibody, Immonoconjugates and Radiopharmaceuticals*, vol. 4, No. 4, 1991, pp. 915–922.

Folkes, L., et al., "Peroxidase–Catalyzed Effects of Indole–3–Acetic Acid and Analogues on Lipid Membranes, DNA, and Mammalian Cells, in Vitro," *Biochemical Pharmacology*, vol. 57, 1999, pp. 375–382.

Candeias, L., et al., "Amplification of Oxidative Stress by Decarboxylation: A New Strategy in Anti–Tumor Drug Design," *Biochemical Society Transactions*, 23, 1995, p. 262.

Job, D., et al., "Substituent Effect on the Oxidation of Phenols and Aromatic Amines by Horseradish Peroxidase Compound I," *Eur. J. Biochem.*, 66, 1976, pp. 607–614.

Still, C., et al., "Inhibitory Oxidation Products of Indole–3–Acetic Acid," *The Journal of Biological Chemistry*, vol. 240, No. 6, Jun. 1965, pp. 2612–2618.

Fukuyama, T. et al., "Inhibition of Cell Growth by Photo-oxidation Products of Indole–3–Acetic Acid," *The Journal of Biological Chemistry*, vol. 239, No. 7, Jul. 1964, pp. 2392–2397, U.S.A.

Mirsky, I., et al., "Hypoglycemic Action of Indole–3–Acetic Acid by Mouth in Patients with Diabetes Mellitus," *Proc. Soc. Exp. Biol. Med.*, 1956, pp. 109–110.

Pires de Melo, M., et al., "Peroxidase Activity May Play a Role in the Cytotoxic Effect of Indole Acetic Acid," *Photochemistry and Photobiology*, 65, (2), 1997, pp. 338–341.

Pires de Melo, M., et al., "Effect of Indole Acetic Acid on Oxygen Metabolism in Cultured Rat Neutrophil," *Gen. Pharmac.*, vol. 31, No. 4, 1998, pp.573–578, U.S.A.

Huber, B., et al.,"Retroviral–Mediated Gene Therapy for the Treatment of Hepatocellular Carcinoma: An Innovative Approach for Cancer Therapy," *Proc. Natl. Acad. Sci.*, vol. 88, Sep. 1991, pp. 8039–8043, U.S.A.

Culver, K., et al., "In Vivo Gene Transfer with Retroviral Vector–Producer Cells for Treatment of Experimental Brain Tumors," *Science*, vol. 256, Jun. 12, 1992, pp. 1550–1552.

Dalton, S., et al., "Characterization of SAP–1, a Protein Recruited by Serum Response Factor to the c–fos Serum Response Element," *Cell.*,vol. 68, Feb. 7, 1992, pp. 597–612.

Engelhardt, J., et al., "Direct Gene Transfer of Human CFTR into Human Bronchial Epithelia of Xenografts with E1–Deleted Adenoviruses," *Nature Genetics*, vol. 4, May 1993, pp. 27–34.

Carruth, J., "Clinical Applications for Photodynamic Therapy," *J. Photochem. Photobiol.*, 9, 1991, pp. 396–397.

Kennedy, J., et al., "New Trends in Photobiology (Invited Review)," *J. Photochem. Photobiol. B. Biol.*, 14, 1992, pp. 275–292.

Morgan, R., et al., "Human Gene Therapy," *Annu. Rev. Biochem.*, 62, 1993, pp. 191–217.

Mizushima, S., et al., "pEF–BOS, A Powerful Mammalian Expression Vector," *Nucleic Acids Research*, vol. 18, No. 17, p. 5322.

Ram, et al., "In Situ Retroviral–Mediated Gene Transfer for the Treatment of Brain Tumors in Rats," *Cancer Research*, 53, Jan. 1, 1993, pp. 83–88.

Regula, J., et al., "Photosensitisation an Photodynamic Therapy of Oesophageal, Duodenal, and Colorectal Tumours Using 5 Aminolaevulinic Acid Induced Protoporphyrin IX–a Pilot Study," *Gut*, 36, 1995, pp. 67–75.

Folkes, L., et al., "Enhancing the Efficacy of Photodynamic Cancer Therapy by Radicals from Plant Auxin (Indole–3–Acetic Acid)," *Cancer Research*, 63, Feb. 15, 2003, pp. 776–779.

Nakane, P., et al., "Peroxidase–Labeled Antibody A New Method of Conjugation," *The Journal of Histochemistry and Cytochemistry*, vol. 22, No. 12, 1974, pp. 1084–1091, U.S.A.

Hudson, L., et al., "Immunochemical Methods," Chapter 9, *Practical Immunology*, $2^{nd}$ Edition, 1976, pp. 205–212, Oxford, United Kingdom.

Greco, O., et al., "Utilising Horseradish Peroxidase for Hypoxia–Targeted Gene Therapy of Cancer," Hypoxia Meeting 2000, Royal Pharmaceutical Society, Lambeth, London.

Greco, O., et al., Utilising Horseradish Peroxidase for Hypoxia–Targed Gene Therapy, AACR poster 1999—American Association for Cancer Research, Apr. 10–14, 1999, Philadelphia, Pennsylvania.

Tupper, J., et al., "Efficacy of the Horseradish Peroxidase/Indole–3–Acetic Acid Combination in an in vitro Tumour Model," Absract at Hypoxia Meeting, Nov. 27, 2002.

Tupper, J., et al., "The Horseradish Peroxidase/Indole–3–Acetic Acid Combination for Enzyme Prodrug Therapy," Meeting, British Cancer Research Meeting, Jun. 30–Jul.3, 2002, Glasgow, United Kingdom.

Folkes, L., "Toward Targeted "Oxidation Therapy" of Cancer: Peroxidase–Catalysed Cytotoxicity of Indole–3–Acetic Acids," *Int. J. Radiation Oncology Biol. Phys.*, vol. 42, No. 4, 1998, pp. 917–920.

Tupper, J., et al., "Intial in vivo Data from the Horseradish Peroxidase/Indole–3–Acetic Acid Enzyme Prodrug Combination," Abstract at BIR Meeting, Nov.1, 2002.

Cancer Research Scientific Yearbook 2001–02, pp.36–39, May 2002.

Extract from Gray Laboratory Annual Report, 1996.

Extract from Gray Laboratory Annual Report 1998, pp. 27–28.

Extract from Gray Laboratory Annual Report 1999.

Extract from Gray Laboratory Annual Report 1997.

Batcho, A.D., et al., "Indoles from 2–MethylnitroBenzenes by Condensation with Formamide Acetals Followed by Reduction: 4–Benzyloxyindole." *Org. Synth.*, vol. 63, pp. 214–225.

Greco, O., "Pharmacology and Experimental Therapeutics," *Proceedings of the American Association for Cancer Research*, vol. 40, Mar. 1999, p. 478.

Greco, O., "Pharmacology and Experimental Therapeutics", *Proceedings of the American Association for Cancer Research*, vol. 41, Mar. 2000, p. 733.

Greco, O., "*Immunology/Experimental and Preclinical 1*", *Proceedings of the American Association for Cancer Research*, vol. 42, Mar. 2001, p. 27.

Greco, O., "Experimental/Molecular Therapeutics 36", *Proceedings of the American Association for Cancer Research*, vol. 43, Mar. 2002, p. 857.

Greco, O., "Utilising Horseradish Peroxidase for Hypoxia–Targeted Gene Therapy," Abstract at Symposium on "Tissue Hypoxia," Mar. 23, 2000, at the Royal Pharmaceutical Society, Lambeth, London (AAR 2000).

Folkes, L.K. et al., "Toward Targeted Oxidation Therapy of Cancer: Peroxidase–Catalysedcytotoxicity of Indole–3–Acetic Acids", Intl. Journal of Radiation: Oncology Biology Physics, Pergamon Press, US, vol. 42, No. 4, Nov. 1, 1998, pp. 917–920, XP001022013, ISSN: 0360–3016.

Candeias, L.P. et al: "Factors Controlling the Substrate Specificity of Peroxidases: Kinetics and Thermodynamics of the Reaction of Horseradish Peroxidase Compound I with Pehnols and Indole–3–acetic Acids", Biochemistry, Vo.I. 36, 1997, pp. 7081–7085, XP002181164 (abstract) Table 1.

Candeias, L.P. et al: Rates of Reaction of Indoleacetic Acids with Horseradish Peroxidase Compound I and Their Dependence on the Redox Potentials:, Biochemistry, vol. 35, 1996, pp. 102–108, XP002181165 (abstract) Tables 2, 3.

* cited by examiner

USE OF INDOLE-3-ACETIC ACID DERIVATIVES IN MEDICINE

This invention relates to derivatives of indole-3-acetic acid (IAA) and their use as pharmaceuticals, in particular for treating neoplastic disease.

Indole-3-acetic acid:

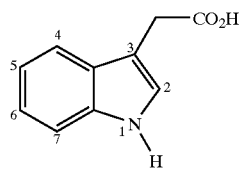

is a naturally-occurring plant growth phytohormone which has been extensively studied. As long ago as 1956, its effects in humans were studied, and it was shown that single doses of 0.1 g/kg were non-toxic (Mirsky A and Diengott D, Hypoglycemic action of indole-3-acetic acid by mouth in patients with diabetes mellitus, *Proc. Soc. Exp. Biol. Med.* 93: 109–110, 1956). In 1964, it was found that its photo-oxidation products acted as growth inhibitors of microorganisms (Still C, Fukuyama T and Moyed H, Inhibitory Oxidation Products of Indole-3-acetic acid, J. Biological Chemistry, 240, 6, 2612–2618, 1964).

More recently, there has been interest in using indole-3-acetic acid as a prodrug in combination with horseradish peroxidase (HRP). IAA is viewed as a suitable prodrug as it is non-toxic in its stable form, it is not oxidised to any substantial extent by the human body's natural peroxidases, but it is readily oxidised by HRP. HRP, and other peroxidases, are enzymes which can be delivered to the desired site of activity by methods discussed below, such as, ADEPT and GDEPT.

For example, the enzyme may be linked to a monoclonal-antibody so that it can bind to an extra-cellular tumour-associated antigen. This approach to cancer therapy, often referred to as "antibody directed enzyme/prodrug therapy" (ADEPT) is disclosed in WO88/07378, and is currently in Phase II clinical trials.

A variation on ADEPT is "polymer directed enzyme/prodrug therapy" (PDEPT), in which the compound to be targeted, for example the enzyme, is bound to a water soluble, biocompatible and non-immunogenic polymer. This polymer localises in the tumour due to the blood vessels in tumours being leaky, allowing the polymer-bound molecules to enter the extra-cellular spaces in tumours, which does not occur very readily in normal tissues. Clearance from the tumour is slow due to lack of lymphatic drainage, allowing the localised enzyme-polymer to activate the prodrug. PDEPT is described in more detail in "The Role of Polymer Conjugates in the Diagnosis and Treatment of Cancer", Duncan R et al, *STP Pharma Sciences* 6:237–263, 1996), and has recently completed Phase I trials in administering cytotoxic drugs (e.g. doxorubicin) to tumours (Vasey P A et al, *Phase I clinical and pharmacokinetic study of PK1* [N-(2-hydroxypropyl) methacrylamide copolymer doxorubicin]: first member of a new class of chemotherapeutic agents-drug-polymer conjugates, *Clin. Cancer Res* 5:83–94, 1999).

A further therapeutic approach termed "virus-directed enzyme prodrug therapy" (VDEPT) is where tumour cells are targeted with a viral vector carrying a gene encoding the relevant enzyme. The gene may be transcriptionally regulated by tissue specific promoter or enhancer sequences. The viral vector enters tumour cells and expresses the enzyme, thereby converting the prodrug into the active drug within the tumour cells (Huber et al., *Proc. Natl. Acad. Sci. USA* (1991) 88, 8039).

Alternatively, non-viral methods for the delivery of genes have been used. Such methods include calcium phosphate co-precipitation, microinjection, liposomes and derivatives, electroporation, direct DNA uptake, and receptor-mediated DNA transfer. These are reviewed in Morgan & French, *Annu. Rev. Biochem.*, 1993, 62;191. The term "GDEPT" (gene-directed enzyme prodrug therapy) is used to include both viral and non-viral delivery systems. GDEPT is also currently in clinical trials.

Photodynamic therapy (PDT) involves the use of light to activate molecules in order to produce toxic species. The majority of current and proposed technique's use singlet oxygen as the toxic species derived from the reaction of a photosensitizer with cellular oxygen. The technique's main drawback is that it does not work in anoxic tumours and that the photosensitizers are not readily excreted by the body, and therefore patients treated with PDT remain sensitive to light for a considerable period after treatment.

The mechanism of action of HRP on IAA is proposed to be as follows (Peroxidase-catalysed effects of Indole-3-acetic acid and analogues on lipid membranes, DNA, and mammalian cells in vitro, Folkes L et al, *Biochemical Pharmacology*, 57, 375–382, 1999):

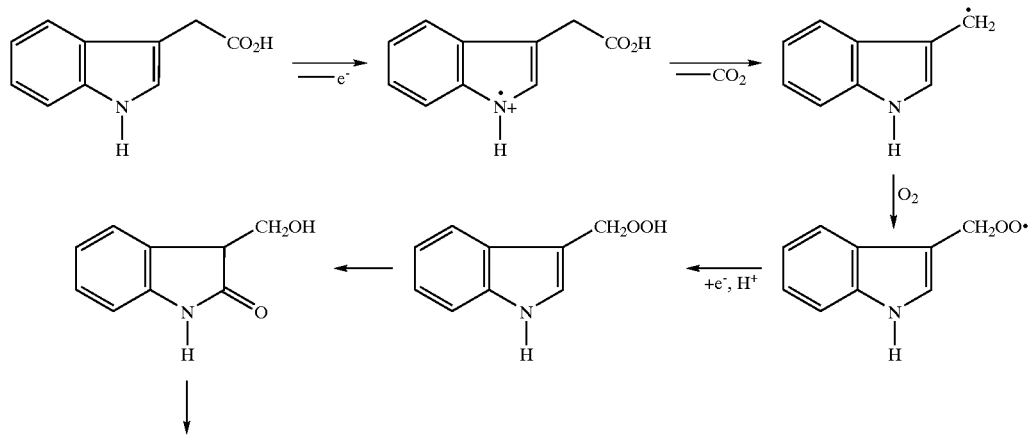

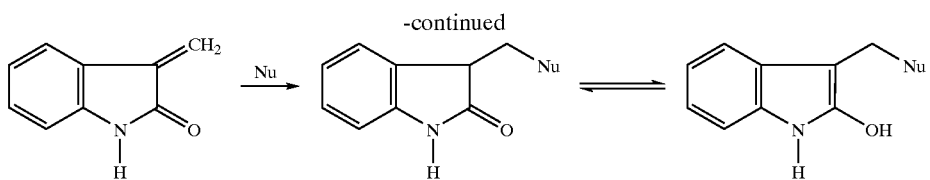

In the diagram above, Nu refers to a cellular nucleophilic centre found in, e.g. DNA or proteins. In the absence of oxygen, the skatole radical may react with biomolecules.

Unusually, IAA is oxidised by HRP without requiring hydrogen peroxide.

The exact nature of the cytotoxic action of the oxidised derivatives of IAA is not known, although various possible mechanisms have been suggested.

Recent work by the inventors has shown that when the aromatic ring of IAA is substituted by electron donating substituents, such as methoxy, the rate of oxidation by HRP is increased, although cytotoxicity falls.

Surprisingly, the inventors have now found that when the aromatic ring of IAA is substituted by at least one electron withdrawing group, the cytotoxicity of the compounds, when activated by peroxidase, increases. This is particularly surprising in view of the slower reaction between such substituted-IAAs and peroxidase.

Accordingly, a first aspect of the present invention provides the use of compounds of formula (I), or physiologically functional derivatives thereof, in a method of therapy:

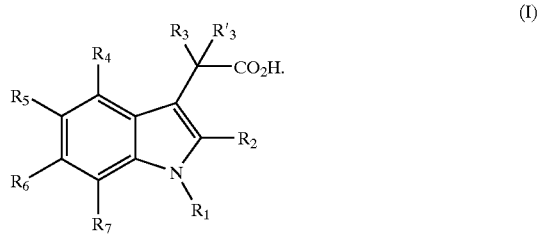

(I)

wherein:

$R_1$, $R_2$, $R_3$ and $R'_3$ are independently selected from H or lower alkyl; and $R_4$, $R_5$, $R_6$ and $R_7$ are independently selected from H, electron withdrawing groups (such as F, Cl, Br, I, $OCF_3$, carboxyl groups, acetal groups, electron deficient aryl groups), lower alkyl groups, lower alkoxy groups, aryl groups or aryloxy groups, wherein at least one of $R_4$, $R_5$, $R_6$ and $R_7$ is selected from an electron withdrawing group.

'Electron-withdrawing' groups are those groups which reduce the electron density in other parts of the molecule. Those groups suitable for use in the present invention include F, Cl, Br, I, $OCF_3$, carboxyl groups, acetal groups and electron deficient aryl groups. The preferred electron withdrawing groups are F, Cl, Br and I, of which F, Cl and Br are most preferred.

'Lower alkyl' in this application means a group having from 1 to 7 carbon atoms, which may be aliphatic or alicyclic, or a combination thereof and which may be saturated, partially unsaturated, or fully unsaturated. This group may bear one or more substituents, selected from halo (i.e. F, Cl, Br, I, preferably F, Cl, Br), carboxyl, acetal, aryl, aryloxy and alkoxy.

Examples of saturated linear lower alkyl groups include, but are not limited to, methyl, ethyl, n-propyl, n-butyl, and n-pentyl (amyl).

Examples of saturated branched lower alkyl groups include, but are not limited to, iso-propyl, iso-butyl, sec-butyl, tert-butyl, and neo-pentyl.

Examples of saturated alicyclic (carbocyclic) lower alkyl groups (also referred to as "$C_{3-7}$ cycloalkyl" groups) include, but are not limited to, unsubstituted groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methycyclopentyl, dimethycyclopentyl, methylcyclohexyl, dimethylcyclohexyl, cyclopropylmethyl and cyclohexylmethyl.

Examples of unsaturated lower alkyl groups which have one or more carbon-carbon double bonds (also referred to as "$C_{2-7}$ alkenyl" groups) include, but are not limited to, ethenyl (vinyl, —CH=$CH_2$), 2-propenyl (allyl, —CH—CH=$CH_2$), isopropenyl (—C($CH_3$)=$CH_2$), butenyl, pentenyl, and hexenyl.

Examples of unsaturated lower alkyl groups which have one or more carbon-carbon triple bonds (also referred to as "$C_{2-7}$ alkynyl" groups) include, but are not limited to, ethynyl (ethinyl) and 2-propynyl (propargyl).

Examples of unsaturated alicyclic (carbocyclic) lower alkyl groups which have one or more carbon-carbon double bonds (also referred to as "$C_3$ "cycloalkenyl" groups) include, but are not limited to, unsubstituted groups such as cyclopropenyl, cyclobutenyl, cyclopentenyl, and cyclohexenyl, as well as substituted groups (e.g. groups which comprise such groups) such as cyclopropenylmethyl and cyclohexenylmethyl.

'Carboxyl' in this application means a group of structure —C(=O)—, and includes carboxylates, acyl groups, amides and acyl halides.

'Carboxylates' means groups of structure —C(=O)OR, where R is H or a carboxyl substituent, for example, a lower alkyl group or a $C_{5-20}$ aryl group, preferably a lower alkyl group. Examples of carboxyl groups include, but are not limited to —C(=O)OH, —C(=O)$OCH_3$, —C(=O)$OCH2CH_3$, —C(=O)OC($CH_3)_3$, and —C(=O)OPh.

'Acyl' in this application means a group of structure —C(=O)R, where R is H or an acyl substituent, for example, a lower alkyl group or a $C_{5-20}$ aryl group, preferably a lower alkyl group. Examples of acyl groups include, but are not limited to, —C(=O)H (formyl), —C(=O)$CH_3$ (acetyl), —C(=O)$CH_2CH_3$ (propionyl), —C(=O)C($CH_3)_3$ (butyryl), and —C(=O)Ph (benzoyl, phenone).

'Amides' in this application means groups of structure —C(=O)$NR_1R_2$, wherein $R^1$ and $R^2$ are independently amino substituents, for example, hydrogen, a lower alkyl group (also referred to as $C_{1-7}$ alkylamino or di-$C_{1-7}$ alkylamino), or a $C_{5-20}$ aryl group, preferably H or a $C_{1-7}$ alkyl group. Examples of amido groups include, but are not limited to, —C(=O)$NH_2$, —C(=O)$NHCH_3$, —C(=O)NH($CH_3)_2$, —C(=O)NH$CH_2CH_3$, and —C(=O)N($CH_2CH_3)_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinocarbonyl.

'Acylhalide' means groups of structure —C(=O)X, wherein X is —F, —Cl, —Br, or —I, preferably —Cl, —Br, or —I.

'Acetal' in this application means a structure —C(OR$^3$)(OR$^4$)—, where the third substituent is as for a carbonyl group (defined above). R$^3$ and R$^4$ are selected from lower alkyl groups, or may together form a divalent alkyl group.

'Alkoxy' in this application means a group of structure —OR, wherein R is an optionally substituted lower alkyl group, wherein the substituent may include halo (F, CL, Br, I) and aryl. Examples of alkoxy groups include, but are not limited to, —OCH$_3$ (methoxy), —OCH$_2$CH$_3$ (ethoxy), —OC(CH$_3$)$_3$ (tert-butoxy), —OBn (benzyloxy), and —OCH$_2$F (fluoromethoxy).

'Aryl' in this application means a monovalent moiety obtained by removing a hydrogen atom from a ring atom of a $C_{5-20}$ aromatic compound (also known as a $C_{5-20}$ aryl group), said compound having one ring, or two or more rings (e.g. fused), and having from 5 to 20 ring atoms. Preferably, each ring has from 5 to 7 ring atoms.

The ring atoms may be all carbon atoms, as in "carboaryl groups", in which case the group may conveniently be referred to as a "$C_{5-20}$ carboaryl" group.

Examples of aryl groups which do not have ring heteroatoms (i.e. $C_{5-20}$ carboaryl groups) include, but are not limited to, those derived from benzene (i.e. phenyl), naphthalene, anthracene, phenanthrene, and pyrene.

Alternatively, the ring atoms may include one or more heteroatoms, including but not limited to oxygen, nitrogen, and sulfur, as in "heteroaryl groups." In this case, the group may conveniently be referred to as a "$C_{5-20}$ heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$ heteroaryl groups include, but are not limited to, $C_5$ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, and oxatriazole; and $C_6$ heteroaryl groups derived from isoxazine, pyridine (azine), pyridazine (1,2-diazine), pyrimidine (1,3-diazine; e.g. cytosine, thymine, uracil), pyrazine (1,4-diazine), triazine, tetrazole, and oxadiazole (furazan).

Examples of $C_{5-20}$ heterocyclic groups (including $C_{5-20}$ heteroaryl groups) which comprise fused rings, include, but are not limited to, those derived from quinoline, isoquinoline, purine (e.g., adenine, guanine), benzimidazole, carbazole, fluorene, phenoxathiin, benzofuran, indole, isoindole, quinoxaline, phenazine, phenoxazine, xanthene, acridine, and phenothiazine.

'Electron deficient aryl groups' in this application means an aryl group which is electron withdrawing, and includes heteroaryl groups. An example of an electron deficient aryl group is para-chlorophenyl.

'Aryloxy' in this application means a group of structure —OR, wherein R is an aryl group. An examples of an aryloxy group is —OPh (phenoxy).

Physiologically functional derivatives of prodrugs include salts, amides and esters. Esters include carboxylic acid esters in which the non-carbonyl moiety of the ester grouping is selected from straight or branched chain $C_{1-6}$ alkyl (e.g. methyl, n-propyl, n-butyl or t-butyl); or $C_{3-6}$ cyclic alkyl (e.g. cyclohexyl). Salts include physiologically acceptable base salt, e.g. derived from an appropriate base, such as alkali metal (e.g. sodium, alkaline earth metal (e.g. magnesium) salts, ammonium and NR$_{14}$ (where R" is $C_{1-4}$ alkyl) salts. Other salts include acid addition salts, including the hydrochloride and acetate salts. Amides include non-substituted and mono and di substituted derivatives. Such derivatives may be prepared by techniques known per se in the art of pharmacy.

It is preferred that the balance, or overall effect, of the substituents $R_4$, $R_5$, $R_6$ and $R_7$ is electron withdrawing.

The following preferences for the groups $R_1$, $R_2$, $R_3$, $R'_3$, $R_4$, $R_5$, $R_6$ and $R_7$ may be independent of each other or may be in any combination with each other.

$R_1$ and $R_2$ are preferably selected from H or optionally substituted saturated lower alkyl groups, more preferably optionally substituted saturated linear lower alkyl groups, more particularly methyl or ethyl. The most preferred group for $R_1$ and $R_2$ is H.

If the lower alkyl group of $R_1$ is substituted, the substituent is preferably one which aids solubility of the whole compound, such as morpholino or piperazinyl.

$R'_3$ is preferably H. $R_3$ is preferably selected from H or optionally substituted saturated lower alkyl groups, more preferably optionally substituted saturated linear lower alkyl groups, more particularly methyl or ethyl. The most preferred group for $R_3$ is H, so that in combination $R_3$ and $R'_3$ are both H.

It is preferred that one or two, more preferably one, of $R_4$, $R_5$, $R_6$ and $R_7$ are independently selected from electron withdrawing groups.

If one or more of $R_4$, $R_5$, $R_6$ and $R_7$ are not H or an electron withdrawing groups, they are preferably selected from optionally substituted saturated lower alkyl groups, more preferably optionally substituted saturated linear lower alkyl group and most preferably unsubstituted linear lower alkyl groups, more particularly methyl or ethyl.

It is most preferred that one of $R_4$, $R_5$, $R_6$ and $R_7$ is an electron withdrawing group and the rest are H, and in particular that $R_5$ is the electron withdrawing group.

One preferred aspect of the invention is the compounds of formula (I) which exhibit a greater cytotoxic effect (i.e. leave less surviving cells when tested under identical conditions) on a neoplastic cell line in vitro than indole-3-acetic acid. Preferably the cell line is hamster lung fibroblast V79 from the European Tissue Culture Collection.

A second aspect of the present invention provides the use of a compound of formula (I) as defined in the first aspect of the invention in the manufacture of a medicament for treating neoplastic disease.

A third aspect of the present invention provides the use of compounds of formula (I) as defined in the first aspect of the invention in conjunction with a conjugated peroxidase enzyme (for example and preferably horseradish peroxidase) in methods of ADEPT and PDEPT therapy, or in conjunction with a vector encoding and capable of expressing a peroxidase enzyme (for example and preferably horseradish peroxidase) in a tumour cell in a method of GDEPT. The drug produced by the action of the peroxidase enzyme on the compounds of formula (I) may be used for the selective killing of oxic and hypoxic tumour cells in methods of treatments of cancers, for example leukaemias and particularly solid cancers including breast, bowel, liver, head and neck, and lung tumours, including small cell carcinoma.

A fourth aspect of the present invention provides the use of compounds of formula (I) as defined in the first aspect of the invention in conjunction with a photosensitizer (e.g. porphyrins, phenothiazines (methylene blue, toluidine blue, thionine), rose bengal, hypericin, phthalocyanines) in methods of photodynamic therapy (PDT).

The preferred embodiments of the second, third and fourth aspects of the present invention may relate to different subsets of compounds of formula (I).

The invention also provides pharmaceutical compositions comprising a compound of formula (I) as defined in the first aspect of the invention together with a pharmaceutically acceptable carrier or diluent.

Synthesis Routes

Figure 1:
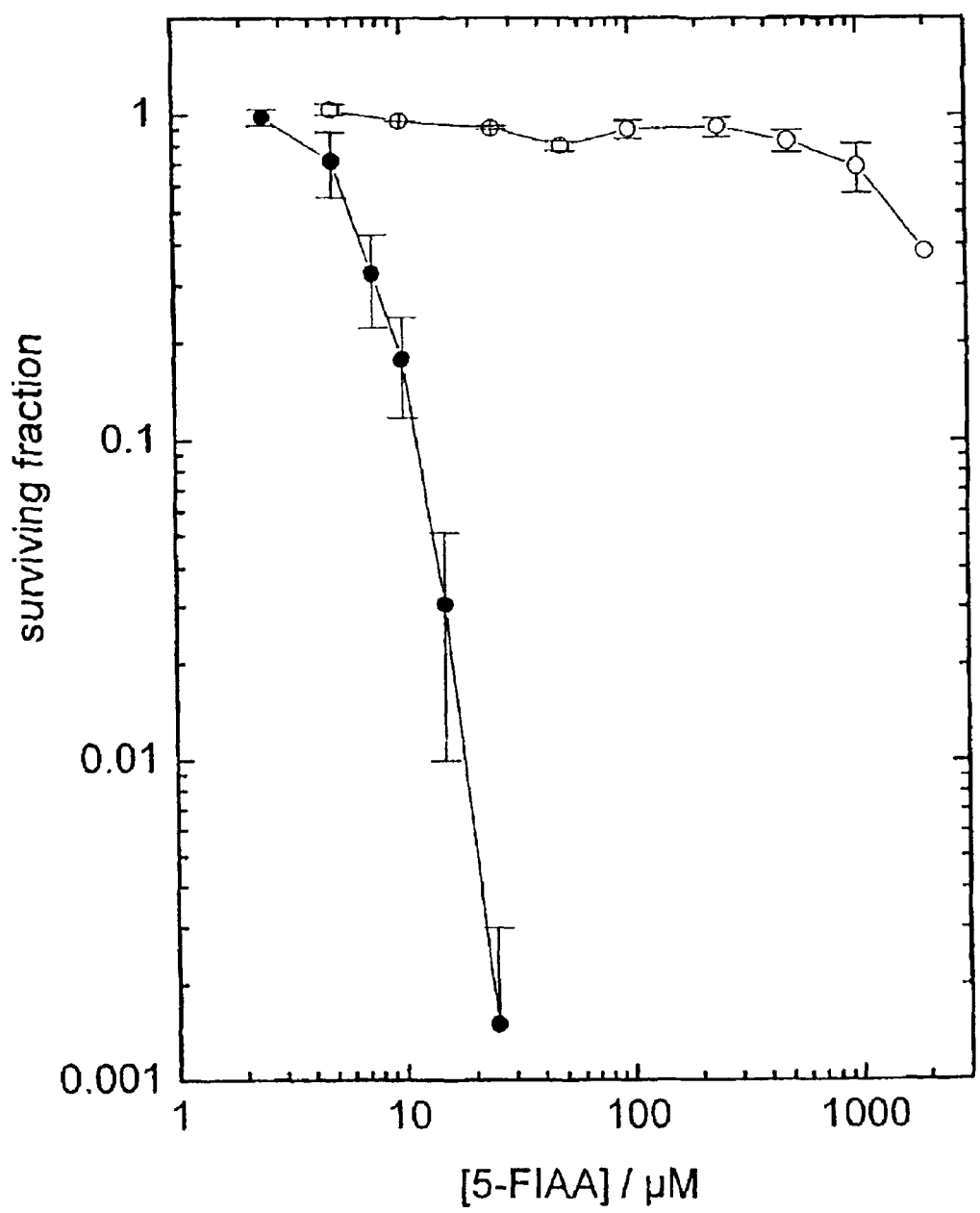
FIG. 1 shows the variation in the surviving fraction of V79 cells against varying concentration of a compound of formula (I), 5-fluoro-indole-3-acetic acid, following 5-hours incubation, with or without HRP (1.2 µg/L).

Compounds of formula (I) may be made by various routes, some of which are outlined below.

Fischer Indole Synthesis

The starting materials for this method are the corresponding phenylhydrazines, which are available commercially or can be synthesised from the corresponding aniline. (KC Engvild, *Acta Chem. Scand. B,* 1977, 31, 338–339; SW Fox, MW Bullock, *J. Am. Chem. Soc.,* 1951, 73, 2756–2759). The overall synthetic method is shown in scheme 1.

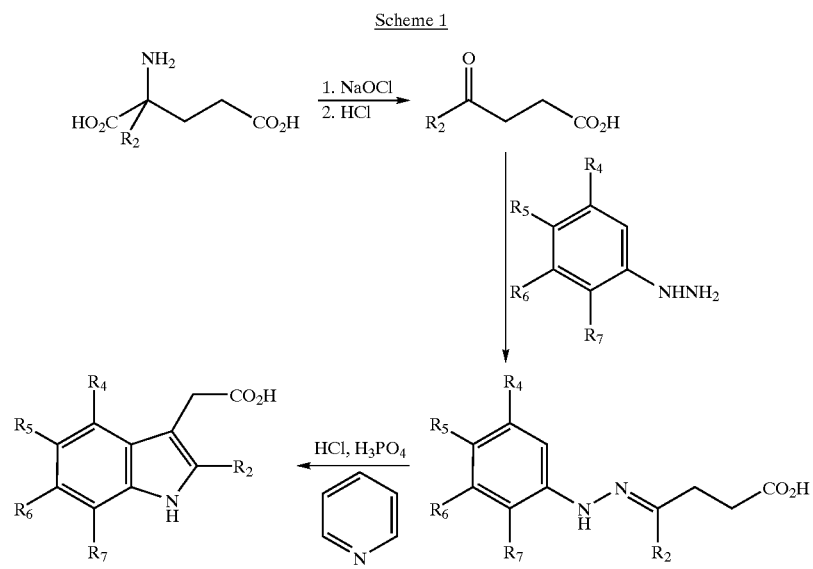

Scheme 1

Side Chain Introduction

If the parent indole is available (e.g. 7-chloroindole) or synthesised by one of the routes below, the compound of formula (I) can be synthesised by introduction of the acetate side chain onto the parent indole, using the reagents shown in Scheme 2. (RD Dillard et al., *J. Med. Chem,* 1996, 39, 5119–5136)

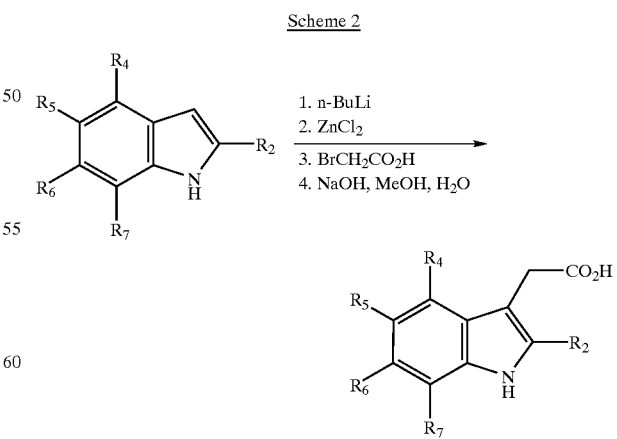

Scheme 2

Halogenated Compounds

The parent indoles of compounds in which at least one of $R_4$, $R_5$, $R_6$, and $R_7$ are halogens can in particular be prepared by the Leimgrüber-Batcho method, see Scheme 3 (AD Batcho, W Leimgrüber, *Org. Synth.*, 1985, 63, 214–225) or the Bartoli method, see Scheme 4 (G Bartoli, G Palmieri, *Tet. Lett.*, 1989, 30, 2129–2132).

Scheme 3

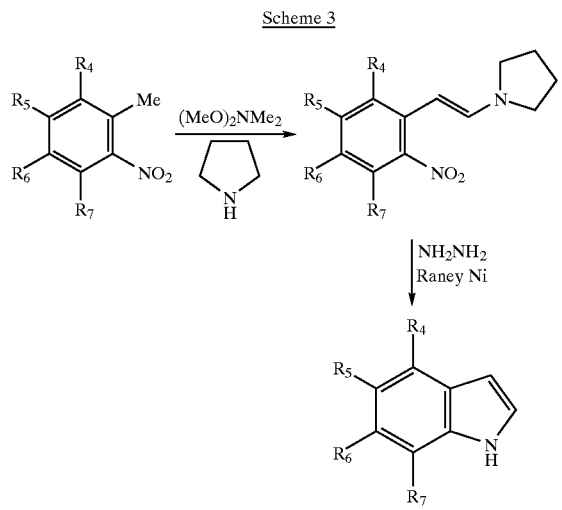

Scheme 4

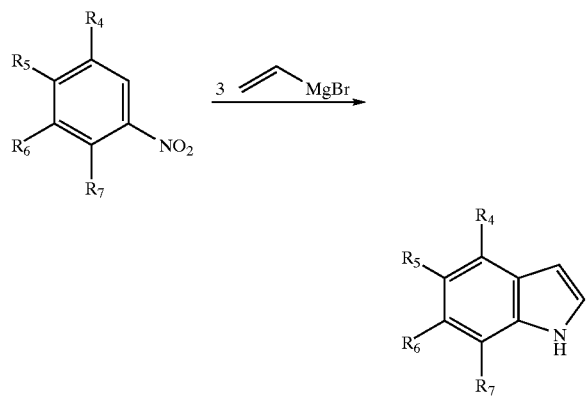

Aryl-substituted compounds

Indoles where one or more of $R_4$ to $R_7$ is an aryl group can be made by Suzuki coupling of the appropriate arylboronic acid with the corresponding bromoindole, using a variation on the method employed by Carrera (GM Carrera, GS Sheppard, *Synlett*, 1994, 93–94) This is outlined in Scheme 5.

Scheme 5

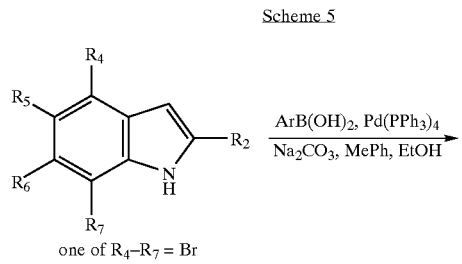

one of $R_4$–$R_7$ = Br

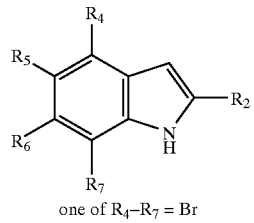

one of $R_4$–$R_7$ = Br $R_1$ can be introduced at any appropriate stage in the above synthesis routes by the deprotonation of the indole nitrogen by a suitable base (for example, sodium hydride, sodium carbonate), followed by reaction with an appropriate electrophile, preferably in the form RX, where X is a halogen (for example, iodomethane).

$R_3$ may be introduced by reaction of the substituted IAA ($R_3$=H) with the base LDA, followed by an electrophile (AH Katz et al, *Journal of Medicinal Chemistry*, 1988, 31, 1244–50). Alternatively, the desired side chain could be introduced onto the parent indole, by for example, the reaction of the parent indole with sodium hydroxide, ethanol and lactonitrile to give the α-methyl IAA (Erdtmann et al, *Acta Chemica Scandinavia.*, 1954, 8, 119–123).

GDEPT

Vector Systems

In general, the vector for use in GDEPT therapies may be any suitable DNA or RNA vectors.

Suitable non-viral vectors include cationic liposomes and polymers. Suitable viral vectors include those which are based upon a retrovirus. Such vectors are widely available in the art. Huber et al. (ibid) report the use of amphotropic retroviruses for the transformation of hepatoma, breast, colon or skin cells. Culver et al. (*Science* (1992) 256; 1550–1552) also describe the use of retroviral vectors in GDEPT. Such vectors or vectors derived from them may also be used. Other retroviruses may also be used to make vectors suitable for use in the present invention. Such retroviruses include Rous sarcoma virus (RSV).

Englehardt et al. (*Nature Genetics* (1993) 4; 27–34) describe the use of adenovirus-based vectors in the delivery of the cystic fibrosis transmembrane conductance product (CFTR) into cells, and such adenovirus-based vectors may also be used. Vectors utilising adenovirus promoter and other control sequences may be of particular use in delivering a system according to the invention to cells in the lung, and hence useful in treating lung tumours.

Other vector systems including vectors based on the Molony murine leukaemia virus are known (Ram, Z et al., *Cancer Research* (1993) 53; 83–88; Dalton & Treisman, *Cell* (1992) 68; 597–612). These vectors contain the Murine Leukaemia virus (MLV) enhancer cloned upstream at a β-globin minimal promoter. The β-globin 5' untranslated region up to the initiation codon ATG is supplied to direct efficient translation of the enzyme.

Suitable promoters which may be used in vectors described above, include MLV, (cytomegalovirus) CMV, RSV and adenovirus promoters. Preferred adenovirus promoters are the adenovirus early gene promoters. Strong mammalian promoters may also be suitable. An example of such a promoter is the EF-1α promoter which may be obtained by reference to Mizushima and Nagata ((1990), *Nucl. Acids Res.*, 18; 5322). Variants of such promoters retaining substantially similar transcriptional activities may also be used.

Other suitable promoters include tissue specific promoters, and promoters activated by small molecules, hypoxia or X-rays. The use of hypoxia regulated gene expression for gene therapy is described in EP-A-0745131.

HRP is the enzyme of choice for the activation of compounds of formula (I). Other suitable peroxidases include tobacco peroxidase, peanut peroxidase, lignin peroxidase, ascorbate peroxidase, bacterial catalase-peroxidases, yeast cytochrome c peroxidase and *Coprinus cinereus* (*Arthomyces ramosus, Coprinus macrorhizus*) peroxidase. Synthetic peroxidases, e.g. oxoiron(IV)tetra(N-methylpyridyl)porphyrins or microperoxidases may also be used. Microperoxidases may be advantageous as they are small proteins, and thus less likely to cause immunological problems. The enzymes may be modified by standard recombinant DNA techniques, e.g. by cloning the enzyme, determining its gene sequence and altering the gene sequence by methods such as fusion, truncation, substitution, deletion or insertion of sequences for example by site-directed mutagenesis. Reference may be made to "Molecular Cloning" by Sambrook et al. (1989, Cold Spring Harbor) for discussion of standard recombinant DNA techniques. The modification made may be any which still leaves the enzyme with the ability to catalyse the formation of the radical cation in compounds of formula (I), but alters other properties of the enzyme, for example its rate of reaction, selectivity or immunological properties.

In addition, small truncations in the N- and/or C-terminal sequence may occur as a result of the manipulations required to produce a vector in which a nucleic acid sequence encoding the enzyme is linked to the various other vector sequences.

HRP has been expressed in target cells by transfecting a construct (pRK34-HRP) in which HRP c-DNA is fused to the signal sequence for the human growth hormone and the KDEL retention motif (Connolly CN, Futter CE, Gibson A, et al., Transport into and out of the Golgi complex studied by transfecting cells with cDNAs encoding horseradish peroxidase. *J. Cell Biol.* 1994; 127: 641–652). The resulting HRP has been shown to activate indole-3-acetic acid and produce toxic compounds (Greco, O. et al. Development of an enzyme/prodrug combination for gene therapy of cancer, *Proc. Amer. Assoc. Cancer Res.*, 40, 478 (1999)).

ADEPT

For applications in ADEPT systems, an antibody directed against a tumour specific marker is linked to the relevant enzyme, which may be modified as described above. The antibody may be monoclonal or polyclonal. For the purposes of the present invention, the term "antibody", unless specified to the contrary, includes fragments of whole antibodies which retain their binding activity for a tumour target antigen. Such fragments include Fv, F(ab') and F(ab')$_2$ fragments, as well as single chain antibodies. Furthermore, the antibodies and fragments thereof may be humanised antibodies, e.g. as described in EP-A-239400.

The antibodies may be produced by conventional hybridoma techniques or, in the case of modified antibodies or fragments, by recombinant DNA technology, e.g. by the expression in a suitable host vector of a DNA construct encoding the modified antibody or fragment operably linked to a promoter. Suitable host cells include bacterial (e.g. *E. coli*), yeast, insect and mammalian cells. When the antibody is produced by such recombinant techniques the enzyme may be produced by linking a nucleic acid sequence encoding the enzyme (optionally modified as described above) to the 3' or 5' end of the sequence of the construct encoding the antibody or fragment thereof.

PDEPT

In order for the PDEPT approach to be followed, the chosen peroxidase must be bound to a polymer which is water soluble, biocompatible, non-immunogenic and which does not eliminate the activity of the enzyme. PDEPT is likely to present less severe immunogenic effects than ADEPT due to the masking of the foreign enzyme by the polymer. HRP has been successfully bound to polyethylene glycol (PEG), as well as other polymers (Fortier G and Laliberté M, "Surface modification of horseradish peroxidase with polyethylene glycol(s) of various molecular masses" *Biotechnol Appl Biochem.* 17:115–130, 1993; Laliberté M, et al, Surface modification of horseradish peroxidase with polyethylene glycol(s) of various molecular masses (Mr): relationship between the Mr of polyethylene glycol and the stability of horseradish peroxidase-poly (ethylene glycol) adducts under various denaturing conditions. *Biotechnol Appl. Biochem* 20:394–413, 1994

PDT

The activation process in PDT can be highly site specific.

The direction and width of a laser beam can be controlled with great precision. Therefore, it can act upon a very limited area, minimising damage to neighbouring tissue.

Highly reactive and thus cytotoxic species can also result from relatively low energy activations. For example, a reactive excited state of molecular oxygen, the singlet state, differs in only 90 kJ/mol from its ground triplet state. However, this enables sufficient concentrations of the toxic species to be formed by those sensitisers which absorb at wavelengths longer than 600 nm, (Carruth, J. A. S., Clinical applications for photodynamic therapy, *J Photochem Photobiol* (1991) 9, 396–397).

The main limitation of this approach arises from the physics of light itself and its interaction with human tissue. The ability of light to penetrate tissue has been found to be wavelength-dependent. Penetrating ability increases with increasing wavelength but limitations arise due to light scattering and reflection. In biological tissues the scattering coefficient, for example of red light, is much greater than the absorption coefficient, (Carruth, J. A. S., Clinical applications for photodynamic therapy, *J Photochem Photobiol* (1991) 9, 396–397; Kennedy, J. C. And Pottier, R. H, Endogenous protoporphyrin IX, a clinical useful photosensitizer for photodynamic therapy, *J Photochem Photobiol* (1992) 14, 275–292). As a result, photons entering the tissue are scattered several times before they are either absorbed or diffused. Although this might be expected to increase the energy delivered to certain areas, internal reflection results in an exponential decrease of energy flux with increasing distance from the tissue-air interface. These limitations have been partially overcome in the treatment of relatively bulky tumours or when deeper penetration is necessary by the use of multiple interstitial optical fibres.

Several tumour types have been identified as potential targets for PDT. They include head and neck tumours, carcinomas of the bronchus, malignant brain tumours, superficial tumours of the bladder and vascular disease, which have all shown promising responses in the clinic (Regula, J., Mac Roberts, A. J., Gorchein, A., Buonaccorsi, Thorpe, S. M., Spencer, G. M., Hartfield, A. R. W. and Bown, S. G., Photosensitisation and photodynamic therapy of oesophageal, duodenal and colorectal tumours using 5-aminoleavulic acid induced protoporphyrin IX-a pilot study, *Gut* (1995) 36, 67–75).

Apoptosis induction in human tumour cells by photoproducts of indole-3-acetic acid sensitized by riboflavin has recently been described (Edwards, A. M., et al. Apoptosis induction in nonirradiated human HL-60 and murine NSO/2 tumor cells by photoproducts of indole-3-acetic acid and riboflavin. *Photochemisty and Photobiology,* 70, 645–649, 1999).

The use of compounds of formula (I) enhances PDT. In PDT, photolysis of photosensitizers P, equation (1), results in the reaction of the generated triplet excited state $^3P^*$ with ground state oxygen, producing toxic singlet oxygen, equation (2). One drawback with conventional PDT is that no toxicity occurs in anoxia. Without wishing to be bound by theory, a compound of formula (I), illustrated as IAA below, is oxidised by $^3P^*$ to generate an indole radical cation, equation (3) which, as discussed above, leads to toxic products, with or without the involvement of oxygen.

$$P + h\nu \rightarrow {}^3P^* \quad (1)$$

$$^3P^* + O_2 \rightarrow P + {}^1O_2 \quad (2)$$

$$^3P^* + IAA \rightarrow P + IAA.+ \quad (3)$$

The combination, either in aerobic or anoxic conditions, of a compound of formula (I) with a photosensitizer should result in a lower concentration of photosensitizer being needed to achieve the same toxicity. This would reduce the normal tissue damage from light exposure after treatment, which can occur up to several weeks after treatment. The sensitizing effects of IAA derivatives should last only for a few hours, until the IAA is excreted.

The technique of PDT as discussed above can be used by employing a combination of appropriate compounds of formula (I) and photosensitizers. The preferred wavelength of light used is 500 to 800 nm.

Applications of the Invention

Compounds of the invention can be used in vitro or in vivo for a range of applications. For example, for GDEPT a number of vector systems for the expression of peroxidase in a cell have been developed. The further development of such systems (e.g. the development of promoters suitable for specific cell types) requires suitable candidate prodrugs capable of killing cells when activated by peroxidase. Prodrug compounds of formula (I) susceptible to peroxidase may be used in such model systems. The model systems may be in vitro model systems or in vivo xenograft model systems comprising for example human tumour cells implanted in nude mice.

Compounds of formula (I) in conjunction with photosensitizers activated by light having a wavelength between 500 and 800 nm may be tested in vitro with other suitable forms of activation against panels of different tumour cell types to determine efficacy against such tumour cells. The efficacy of compounds of the invention against a range of tumour cell types may be used as points of reference for the development of further antitumour compounds.

Compounds of formula (I) may also be used in a method of treatment of the human or animal body. Such treatment includes a method of treating the growth of neoplastic cells in a patient with neoplastic disease which comprises administering to a patient in need of treatment compounds offormula (I) as part of an ADEPT, GDEPT, PDEPT or PDT system where neoplastic diseases include leukaemia and solid tumours such as ovarian, colonic, lung, renal, breast, bowel, head and neck, CNS and melanomas.

It will be understood that where treatment of tumours is concerned, treatment includes any measure taken by the physician to alleviate the effect of the tumour on a patient. Thus, although complete remission of the tumour is a desirable goal, effective treatment will also include any measures capable of achieving partial remission of the tumour as well as a slowing down in the rate of growth of a tumour including its metastases. Such measures can be effective in prolonging and/or enhancing the quality of life and relieving the symptoms of the disease.

Therapies

Methods of ADEPT, GDEPT and PDEPT will now be described. The basis of PDT has been described above, but the information on the administration of products below also applies to this type of therapy.

ADEPT Therapy

The antibody/enzyme conjugate for ADEPT can be administered simultaneously with the prodrug but it is often found preferable, in clinical practice, to administer the enzyme/antibody conjugate before the prodrug, e.g. up to 72 hours or even 1 week before, in order to give the enzyme/antibody conjugate an opportunity to localise in the region of the tumour target. By operating in this way, when the prodrug is administered, conversion of the prodrug to the cytotoxic agent tends to be confined to the regions where the enzyme/agent conjugate is localised, i.e. the region of the target tumour. In this way, the premature release of the compound produced by the action of the peroxidase on the prodrugs of the present invention is minimised.

In ADEPT the degree of localisation of the enzyme/agent conjugate (in terms of the ratio of localized to freely circulating active conjugate) can be further enhanced using the clearance and/or inactivation systems described in WO89/10140. This involves, usually following administration of the conjugate and before administration of the prodrug, the administration of a component (a "second component") which is able to bind to part of the conjugate so as to inactivate the enzyme in the blood and/or accelerate the clearance of the conjugate from the blood. Such a component may include an antibody to the enzyme component of the system which is capable of inactivating the enzyme.

The second component may be linked to a macromolecule such as dextran, a liposome, albumin, macroglobulin or a blood group O erythrocyte so that the second component is restrained from leaving the vascular compartment. In addition, or as an alternative, the second component may include a sufficient number of covalently bound galactose residues, or residues of other sugars such as lactose or mannose, so that it can bind the conjugate in plasma but be removed together with the conjugate from plasma by receptors for galactose or other sugars in the liver. The second component should be designed for use and administered such that it will not, to any appreciable extent, enter the extravascular space of the tumour where it could inactivate localised conjugate prior to and during administration of the prodrug.

In ADEPT systems, the dose of the prodrug and conjugate will ultimately be at the discretion of the physician, who will take into account such factors as the age, weight and condition of the patient. Suitable doses of prodrug and conjugate are given in Bagshawe et al., *Antibody, Immunoconjugates, and Radiopharmaceuticals* (1991), 4, 915–922. A suitable dose of conjugate may be from 500 to 200,000 enzyme units/m$^2$ (e.g. 20,000 enzyme units/m$^2$) and a suitable dose of prodrug may be from about 0.1 to 200 mg/Kg, preferably from about 10 to about 100 mg/Kg per patient per day.

In order to secure maximum concentration of the conjugate at the site of desired treatment, it is normally desirable to space apart administration of the two components by at least 4 hours. The exact regime will be influenced by various factors including the nature of the tumour to be targeted and the nature of the prodrug, but usually there will be an adequate concentration of the conjugate at the site of desired treatment within 48 hours.

The targeting strategy may be enhanced in some combinations of drug and peroxidase by targeted delivery of the hydrogen peroxide co-factor to the tumour. Targeted delivery of either polymer- or antibody-bound glucose oxidase is described by, e.g., Samoszuk M, Emerson J, Nguyen V, et al. "Targeting of glucose oxidase to murine lymphoma allografts"., *Tumor Targeting* (1995) 1, 37–43; Ben-Yoseph O, Ross BD., "Oxidation therapy: the use of a reactive oxygen species-generating enzyme system for tumour treatment.", *Br J Cancer* (1994) 70, 1131–1135.

The antibody/enzyme conjugate may be administered by any suitable route usually used in ADEPT therapy. This includes parenteral administration of the antibody in a manner and in formulations similar to that described below.

PDEPT Therapy

As in ADEPT therapy, the polymer/enzyme conjugate can be administered simultaneously but it is often found preferable, in clinical practice, to administer the polymer/enzyme conjugate before the prodrug, e.g. up to 72 hours or even 1 week before, in order to give the polymer/enzyme conjugate an opportunity to localise in the region of the tumour target, and hence avoid reaction of the enzyme and prodrug not at the desired site of action.

The dosing and administration of the polymer/enzyme and prodrug will be as described above for ADEPT.

GDEPT Therapy

For use of the vectors in therapy, the vectors will usually be packaged into viral particles and the particles delivered to the site of the tumour, as described in for example Ram et al. (ibid). The viral particles may be modified to include an antibody, fragment thereof (including a single chain) or tumour-directed ligand to enhance targeting of the tumour. Alternatively the vectors may be packaged into liposomes. The liposomes may be targeted to a particular tumour. This can be achieved by attaching a tumour-directed antibody to the liposome. Viral particles may also be incorporated into liposomes. The particles may be delivered to the tumour by any suitable means at the disposal of the physician. Preferably, the viral particles will be capable of selectively infecting the tumour cells. By "selectively infecting" it is meant that the viral particles will primarily infect tumour cells and that the proportion of non-tumour cells infected is such that the damage to non-tumour cells by administration of a prodrug will be acceptably low, given the nature of the disease being treated. Ultimately, this will be determined by the physician.

One suitable route of administration is by injection of the particles in a sterile solution. Viruses, for example isolated from packaging cell lines, may also be administered by regional perfusion or direct intratumoral injection, or direct injection into a body cavity (intracaviterial administration), for example by intra-peritoneal injection.

The exact dosage regime for GDEPT will, of course, need to be determined by individual clinicians for individual patients and this, in turn, will be controlled by the exact nature of the prodrug and the cytotoxic agent to be released from the prodrug. However, some general guidance can be given. Chemotherapy of this type will normally involve parenteral administration of modified virus, and administration by the intravenous route is frequently found to be the most practical. The GDEPT approach may be combined with radiotherapy to further enhance efficacy. When GDEPT is combined with radiotherapy, the combination of the compound of formula (I) with the GDEPT system may be considered a radiosensitizer.

In GDEPT systems the amount of virus or other vector delivered will be such as to provide a high enough cellular concentration of enzyme so as to catalyse the efficient conversion of prodrugs to cytotoxins. Typically, the vector will be administered to the patient and then the uptake of the vector by transfected or infected (in the case of viral vectors) cells monitored, for example by recovery and analysis of a biopsy sample of targeted tissue. This may be determined by clinical trials which involve administering a range of trial doses to a patient and measuring the degree of infection or transfection of a target cell or tumour. The amount of prodrug required will be similar to or greater than that for ADEPT systems.

In using a GDEPT system the prodrug will usually be administered following administration of the vector encoding an enzyme. Suitable doses of prodrug are from about 0.1 to 200 mg/Kg, preferably from about 10 to about 100 mg/Kg per patient per day.

Administration of Prodrugs

While it is possible for the compounds of formula (I) to be administered alone, it is preferable to present them as pharmaceutical formulations, for use with any of the above methods. The formulations comprise the compounds, together with one or more acceptable carriers thereof and optionally other therapeutic ingredients, or diluents. The carrier or carriers must be "acceptable" in the sense of being compatible with the other ingredients of the formulation and not deleterious to the recipients thereof, for example, liposomes. Suitable liposomes include, for example, those comprising the positively charged lipid (N[1-(2,3-dioleyloxy)propyl]-N,N,N-triethylammonium (DOTMA), those comprising dioleoylphosphatidylethanolamine (DOPE), and those comprising 3β[N-(n'N'-dimethylaminoethane)-carbamoyl]cholesterol (DC-Chol).

Formulations suitable for parenteral or intramuscular administration include aqueous and non-aqueous sterile injection solutions which may contain anti-oxidants, buffers, bacteriostats, bacteriocidal Antibiotics and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose containers, for examplesealed ampoules and vials, and may be stored in a freeze-dried (lyophilized) condition requiring only the addition of a sterile liquid carrier, for example Water for Injection, immediately prior to use. Injection solutions and suspensions may be prepared extemporaneously from sterile powders, granules and tablets of the kind previously described.

It should be understood that in addition to the ingredients particularly mentioned above, the formulations may include other agents conventional in the art having regard to the type of formulation in question. Of the possible formulations, sterile pyrogen-free aqueous and non-aqueous solutions are preferred.

The doses may be administered sequentially, e.g. at hourly, daily, weekly or monthly intervals, or in response to a specific need of a patient. Preferred routes of administration are oral delivery and injection, typically parenteral or intramuscular injection or intratumoural injection. For methods of PDT dermal or topical administration may be preferred, e.g. subcutaneous injection or creams and ointments, and such methods of administration are well known.

The exact dosage regime will, of course, need to be determined by individual clinicians for individual patients and this, in turn, will be controlled by the exact nature of the compound of formula (I), but some general guidance can be given. Typical dosage ranges generally will be those described above which may be administered in single or multiple doses. Other doses may be used according to the condition of the patient and other factors at the discretion of the physician.

The following examples illustrate the invention.

Experimental Details

All air-sensitive reactions were carried out in a nitrogen atmosphere. Glassware was oven-dried and cooled in an anhydrous atmosphere prior to use. The melting points were determined using a Gallenkamp melting point apparatus, and are uncorrected. NMR spectra (60 MHz) were recorded on a Jeol MY60 spectrometer. Mass spectra were recorded on a Waters Integrity HPLC/MS system.

EXAMPLE 1

General Method for Fischer Indole Synthesis (Engvild KC et al., ibid.) (See Scheme 1 for Outline)

L-Glutamic acid (30 mmol) (or the appropriate derivative) was dissolved in an equimolar quantity of 2M sodium hydroxide and cooled to 0° C. Sodium hypochlorite solution (1 equivalent) was added, and the mixture stirred at 0° C. for 1 hour. 3M hydrochloric acid (3 equivalents) was then added, and the mixture stirred at 55° C. until negative to starch-iodide. The substituted phenylhydrazine hydrochloride (typically 10 mmol) was added to the warm solution, and the mixture stirred for 1 hour whilst cooling to room temperature. The mixture was then extracted with ethyl acetate (3×50 ml), the combined organic extracts dried over magnesium sulfate, and the solvent removed in vacuo to furnish the crude phenylhydrazone.

This product was then dissolved in pyridine (24 ml). Conc. hydrochloric acid (31 ml) was added, followed by 85% phosphoric acid (8–10 ml), and the mixture heated under reflux in an inert atmosphere for 18 hours. The cooled reaction mixture was poured into an equal volume of ice-cold water, and then extracted with diethyl ether (3×75 ml), the combined ether layers dried (MgSO$_4$) and the solvent removed in vacuo to give the crude product, which was purified by recrystallisation from chloroform.

Example 1(a)

5-Chloroindole-3-acetic acid (SR024)

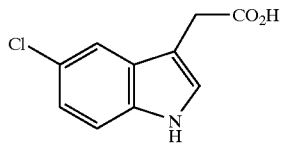

Off-white needles, yield 11%, m.p. 160–161° C. (lit. 158–159° C.); m/z 209 (M$^+$), 164 (M$^+$-CO$_2$H), 128; δH/ppm (CDCl$_3$) 7.66 (1H, s), 7.19 (3H, m), 3.74 (2H, s); found C 57.05%, H 3.82%, N 6.62% (calculated C 57.30%, H 3.85%, N 6.68%).

Example 1(b)

7-Fluoroindole-3-acetic acid (SR022)

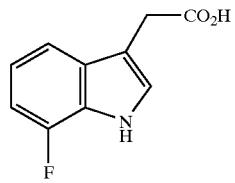

Beige powder, yield 24%, m.p. 159–161° C. (lit. 161–162° C.) m/z 193 (M$^+$), 148 (M$^+$-CO$_2$H); δH/ppm (CD$_3$COCD$_3$) 7.63–6.78 (4H, m, ArH), 3.71 (2H, s, ArCH$_2$).

Example 1(c)

5-Trifluoromethoxyindole-3-acetic acid (SR073)

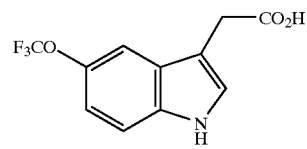

White powder, yield 7%, m.p. 120–122° C.; m/z 259 (M$^+$), 214 M$^+$-Co$_2$H); δH/ppm (CDCl$_3$) 7.43–7.11 (4H, m, ArH), 3.76 (2H, s, ArCH$_2$); found C 50.96%, H 3.18%, N 5.40% (calculated C 50.98%, H 3.11%, N 5.40%).

Example 1(d)

5-Fluoro-2-methylindole-3-acetic acid (SR036)

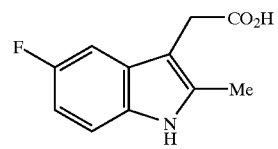

White plates, yield 10%, m.p. 182–184° C. (lit. 179–182° C.); m/z 207 (M$^+$), 162 (M$^+$-CO$_2$H); δH/ppm (CD$_3$COCD$_3$) 7.24–6.60 (3H, m, ArH), 3.65 (2H, s, ArCH$_2$), 2.36 (3H, s, 2-Me).

Example 1(e)

7-Fluoro-5-methylindole-3-acetic acid (SR109)

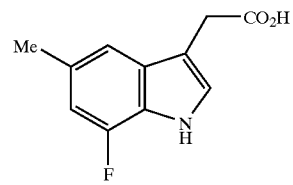

Off-white powder, yield 5%, m.p. 138–140° C.; m/z 207 (M$^+$), 162 (M$^+$-CO$_2$H); δH/ppm (CD$_3$COCD$_3$) 7.29–7.13 (2H, m, ArH), 6.78–6.56 (1H, m, ArH), 3.69 (2H, s, ArCH$_2$), 2.38 (3H, s, 5-Me); found C 62.89%, H 4.86%, N 6.57% (calculated C 63.76%, H 4.86%, N 6.76%).

Example 1(f)

7-Fluoro-4-methylindole-3-acetic acid (SR148)

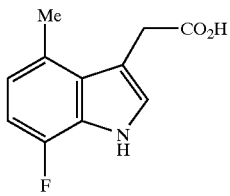

Pale beige powder, yield 4%, m.p. 162–164° C. dec., m/z: 207 (M$^+$), 162 (M$^+$-CO$_2$H); δH/ppm (CD$_3$COCD$_3$) 7.25 (1H, m, ArH), 6.71 (1H, m, ArH), 6.56 (1H, ArH), 3.87 (2H, s, ArCH$_2$), 2.58 (3H, s, 4-CH$_3$),

Example 1(g)

4,6-Dichloroindole-3-acetic acid (SR085)

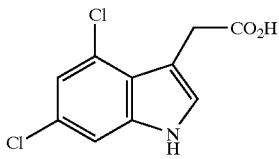

Off-white needles, yield 5%, m.p. 223–224-C (lit. 210–214° C.); m/z 245, 243 (M$^+$), 200, 198 (M$^+$-CO$_2$H); δH/ppm (CD$_3$COCD$_3$) 7.31 (2H, br, ArH [H2, H7]), 6.98 (1H, s, ArH [H5]), 3.97 (2H, s, ArCH$_2$).

Example 1(h)

5-Chloro-7-fluoroindole-3-acetic acid (SR091)

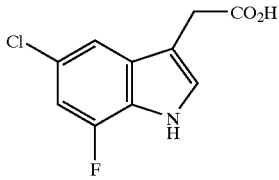

White powder, yield 4%, m.p. 164–166° C.; m/z: 229, 227 (M$^+$), 184, 182 (M$^+$-CO$_2$H); δH/ppm (CD$_3$COCD$_3$) 7.69–6.76 (3H, m, ArH), 3.72 (2H, s, ArCH$_2$); found C 51.57%, H 3.26%, N 6.01%, (calculated C52.77%, B 3.10%, N 6.15%, calculated C$_{10}$H$_7$ClFNO$_2$.0.25H$_2$° C. 51.72%, B 3.26%, N 6.04%).

Example 2

General Method for the Synthesis of Substituted Indole-Acetic Acids From the Parent Substituted Indole
(Dillard, RD, et al., ibid.) (see scheme 2)

The substituted indole, which may be commercially available or synthesised—see below, (typically 5–10 mmol) was dissolved in dry THF (20 ml) and cooled to 0° C. n-Butyllithium (1.1 equivalents) was added, and the mixture stirred at 0° C. for 20 minutes. Zinc chloride (1.1 eq of a 1M solution in diethyl ether) was added, and the mixture stirred at room temperature for 2 hours. Ethyl bromoacetate (1.1 equivalents) was then added over 5 minutes, and the mixture stirred for a further 24 hours. Water (20 ml) was added, and the mixture then extracted with ethyl acetate (3×30 ml), the combined organic extracts dried (MgSO$_4$) and the solution concentrated in vacuo to give the crude product. The crude material was purified by flash column chromatography (3:1 hexane:EtOAc) to give the substituted ethyl indolyl-3-acetate in moderate to low yield, with significant recovery of starting material in most cases. Saponification was effected by heating the ester under reflux for 4 hours in 10% methanolic NaOH (40 ml), then acidifying the mixture with 1M hydrochloric acid, and filtering off the precipitated indole-3-acetic acid. Further purification was achieved by recrystallisation from chloroform.

Example 2(a)

7-Chloroindole-3-acetic acid (SR052)

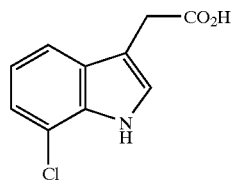

From commercially available starting material) Off-white powder, yield 11%, m.p.164–165-C (lit. 163–165° C.); m/z: 211, 209 (M$^+$), 164 (M$^+$-CO$_2$H); δH/ppm (CD$_3$COCD$_3$) 7.61–6.99 (4H, m, ArH), 3.77 (2H, s, ArCH$_2$); found C 55.51%, H 3.77%, N 6.42% (calculated C 57.30%, H 3.85%, N 6.68%).

Example 3

General Method for Leimgrüber-Batcho Synthesis of the Indole
(Batcho, AD, et al., ibid.) (see scheme 3 for outline)

5 g of the halonitrotoluene was heated with N,N-dimethylformamide dimethyl acetal (1.1 equivalents) and pyrrolidine (1.1 equivalents) until the reaction was judged to be complete by thin layer chromatography. Addition of methanol and concentration under reduced pressure gave the β-pyrrolidinostyrene as either a dark red oil or a crystalline solid, which was then subjected to reduction without further purification.

The β-pyrrolidinostyrene (ca 20 mmol) was dissolved in methanol (50 ml). Raney nickel (0.5 ml of 50% w/v in water) and hydrazine hydrate (30 mmol) were added. The mixture was stirred at 45° C. for 30 minutes, and then a further portion of hydrazine hydrate (30 mmol) was added, and the mixture stirred at 45–50° C. for a further 1 hour. The reaction mixture was filtered through celite and the filtrate evaporated to give a brown oil, which was purified by flash column chromatography (4:1 hexane:EtOAc) to furnish the resulting indole. The indole-3-acetic acid was then synthesised via the ethyl ester, by the method described in example 2 above.

Example 3(a)

4-Fluoroindole-3-acetic acid (SR039)

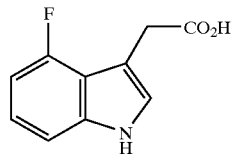

Brownish-white prisms, yield 22%, m.p. 129–131° C. (lit. 128–129° C.); m/z: 193 (M$^+$), 148 (M$^+$-CO$_2$H); δH/ppm (CD$_3$COCD$_3$): 7.23–6.49 (4H, m, ArH), 3.85 (2H, s, ArCH$_2$); found C: 61.87%, H: 4.19%, N: 7.12% (calculated C: 62.18%, H: 4.17%, N: 7.25%).

Example 3(b)

6-Fluoroindole-3-acetic acid (SR043)

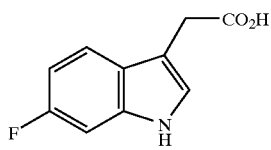

Off-white needles, yield 30%, m.p. 161–163° C. (lit. 165° C.); m/z 193 (M$^+$), 148 (M$^+$-CO$_2$H), 101; δH/ppm (CD$_3$COCD$_3$): 7.61–6.43 (4H, m, ArH), 3.73 (2H, s, ArCH$_2$); found C: 62.08%, H: 4.18%, N: 7.22% (calculated C: 62.18%, H: 4.17%, N: 7.25%).

Example 3(c)

6-Chloroindole-3-acetic acid (SR058)

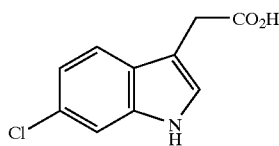

Pale pink plates, yield 14%, m.p. 183–185° C. (lit. 182–184° C.); m/z 209 (M$^+$), 164 (M$^{30}$-CO$_2$H); δH/ppm 7.66–7.06 (4H, m, ArH), 3.71 (2H, s, ArCH$_2$); found C 57.38%, H 3.84%, N 6.67% (calculated C 57.30%, H 3.85%, N 6.68%).

Example 3(d)

6-Bromoindole-3-acetic acid (SR069)

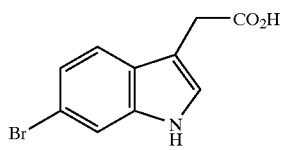

Pale pink lustrous flakes, yield 12%, m.p. 174–176° C. (lit. 172–177° C.); m/z 255,253 (M$^+$), 210,208 (M$^+$-CO$_2$H); δH/ppm (CD$_3$COCD$_3$)7.61–7.12 (4H, m, ArH), 3.76 (2H, s, ArCH$_2$); found C 44.79%, H 3.20%, N 5.11% (calculated C 47.27%, H 3.17%, N 5.51%).

Example 4
General Method for Preparation of Arylindoles by Suzuki Coupling of Bromoindoles
(see scheme 5 for outline)

The appropriate bromoindole (2–5 mmol) and tetrakis(triphenylphosphine)-palladium (0) (5 mol %) were stirred in toluene (15 ml) under nitrogen for 5 minutes, and then the arylboronic acid (1.1 equivalents) in ethanol (4 ml) was added, followed by aqueous sodium carbonate (2 equivalents), and the mixture was then heated at 80° C. under nitrogen for 24 hours. Water (20 ml) was added, and the mixture extracted with ethyl acetate (3×50 ml), the organic layers dried (MgSO$_4$) and the solvent removed in vacuo to give the crude product, which was purified by column chromatography (3:1 hexane:EtOAc) to give the pure arylindole. The indole-3-acetic acid was then synthesised via the ethyl ester, as described in example 2 above.

Example 4(a)

5-(4-Chlorophenyl)indole-3-acetic acid (SR150)

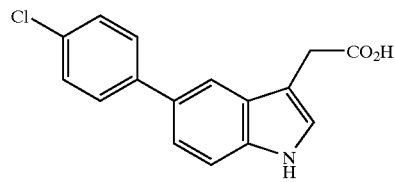

White flakes, yield 15%, m.p. 166–168° C.; m/z 287, 285 (M$^+$), 242, 240 (M$^+$-CO$_2$H); δH/ppm (CD$_3$COCD$_3$) 7.84–7.28 (8H, m, ArH), 3.77 (2H, s, ArCH$_2$); found C 67.05%, H 4.20%, N 4.83% (calculated C 67.26%, H 4.23%, N 4.90%).

Example 5
General Method for Synthesis of Indoles by Bartoli Method (Bartoli G, et al., ibid.) (see scheme 4 for outline)

The appropriate 2-substituted nitrobenzene (typically 5–10 mmol) was dissolved in THF (20 ml) and cooled to −40° C. Vinylmagnesium bromide (3 equivalents of a 1 M solution in ether) was added, and the mixture stirred at −40° C. for 20 minutes, then poured into saturated ammonium chloride solution. The mixture was extracted with diethyl ether (3×50 ml) and the combined organic layers dried (MgSO$_4$) and the solvent removed in vacuo to give the crude indole, which was purified by flash column chromatography. The resulting indole intermediates can be converted to the corresponding indole-3-acetic acids by the method described in example 2.

Example 5(a)

7-Bromoindole-3-acetic acid

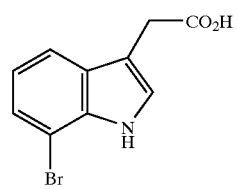

7-bromoindole: Pale brown needles, yield 24%, m.p. 42–44° C. (lit (Aldrich chemical catalogue) 41–44° C.); m/z 197, 195 (M$^+$).

Example 5(b)

6,7-Dichloroindole-3-acetic acid

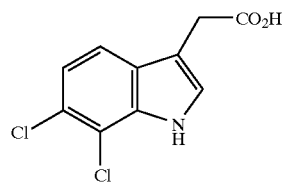

6,7-dicholorindole: Off-white fluffy needles, yield 25%, m.p. 50–52° C.; m/z 185, 187, 189 (ratio 9:6:1, M$^+$), 150, 152 (M$^+$-Cl).

Example 6

N-Substituted INDOLE-3-acetic acids

Example 6(a)

6-Chloro-1-methylindole-3-acetic acid (SR139)

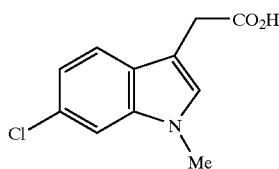

Sodium hydride (0.19 g of 60% suspension in oil) was suspended in dry THF (10 ml). 6-Chloroindole-3-acetic acid (SR058)(100 mg, 0.48 mmol) in THF (5 ml) was added dropwise and the mixture then stirred for 10 minutes. Iodomethane (0.34 g, 2.4 mmol) was then added, and the mixture stirred overnight. Excess sodium hydride was carefully destroyed by dropwise addition of water, and then the mixture was acidified (1M HCl) and extracted with ethyl acetate (3×50 ml), the organic layers dried over $MgSO_4$, and the solvent evaporated to give a brown powder, yield 75 mg, 70%, m.p. 130–132° C. dec.; m/z 225, 223 ($M^+$), 180, 178 ($M^+$-$CO_2H$); δH/ppm 7.46–6.92 (4H, m, Ar—H), 3.77 (3H, s, N—Me), 3.70 (2H, s, $ArCH_2$).

Example 6(b)

5-Fluoro-1-methylindole-3-acetic acid (SR164)

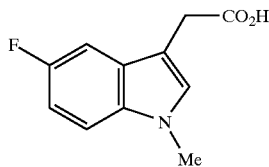

Synthesised as in example 6(a). White needles, yield 52%; m.p 134–136° C.; m/z 207 ($M^+$), 162 ($M^+$-$CO_2H$).

Example 7

Measurements of the Cytotoxic Effects of Treatment with Compounds of Formula (I) and Horseradish Peroxidase (HRP) Using Hamster (V79) and Human (MCF7 and HT29) Cell Lines in vitro Example 7(a)

V79 Cells

Hamster lung fibroblast V79 cells were obtained from the European Tissue Culture Collection. Cells were grown over the weekend in 75 mL tissue culture flats as attached cells in Eagle's Modified Essential Medium (EMEM) supplemented with 10% foetal calf serum, 2 mM L-glutamine, 100 U/mL penicillin and 100 μg/mL streptomycin, and incubated in a humidified incubator at 37° C., in 5% $CO_2$/air. Cells were removed by trypsin treatment when a confluent layer had grown: the cells were washed with phosphate buffered saline and 2 mL of 0.5% w/v porcine trypsin with 0.2% w/v EDTA added for a few minutes at room temperature until the cells were loosened. The trypsin was deactivated by the addition of 10 mL spinner modified EMEM (supplemented with 7.5% foetal calf serum) and the cells allowed to grow in a spinning culture, pre-gassed with 5% $CO_2$/air, maintaining the cells in logarithmic growth.

Cells were prepared for toxicity measurements by counting and plating 200, 2000 or 20,000 cells/6 cm Petri dish in 3 mL EMEM in triplicate for each sample. The cells were allowed to attach for at least 1 hour, then the medium removed and 2 mL phenol red free Hanks' balanced salt solution added, either alone (control) or with 50 or 100 μM of the compound of formula (I) to be tested. HRP (50 μL of 0.048 mg/mL) was added to the test dishes requiring it and the cells left in the incubator for 0, 0.5, 1, 1.5 or 2 hours. After the incubation time the drug was removed, the cells washed with 2 mL Hanks and then 4 mL EMEM added. The cells were allowed to grow for 7 days to colonies of >50 cells. After 7 days the medium was removed and the cells fixed with 75% methanol for 5 minutes. The methanol was then removed and the cells stained with 1% w/v crystal violet for 5 minutes. The cells were washed and colonies counted. Cell survival was determined by calculating the ratio of colonies growing compared to untreated control cells.

In table 1, values are the surviving fraction after 2 hours treatment with the IAA derivatives at the concentrations shown together with HRP (1.2 μg/mL). Unless otherwise indicated (by n=number of individual experiments), the means±the standard errors of three experiments are given. No detectable cytotoxic effects were seen at these times and concentrations with IAA derivative alone or with HRP alone.

TABLE 1

| Compound | Substituent(s) | 50 μM | 100 μM |
| --- | --- | --- | --- |
|  | none* |  | 0.013 ± 0.0048 |
|  | 1-methyl* |  | 0.013 ± 0.005 |
|  | 2-methyl* |  | 0.0042 ± 0.0024 |
|  | 2-methyl-5-methoxy* |  | 0.044 ± 0.013 |
|  | 5-methoxy* |  | 1[b] |
|  | 5-bromo[c] |  | 0.00004 ± 0.00003 |
| SR069 | 6-bromo | 0.0031 ± 0.0023 | 0[a] |
| SR024 | 5-chloro |  | 0.0027 ± 0.0022 |
| SR058 | 6-chloro | 0.00085 (n = 1) | 0[a] |
| SR052 | 7-chloro |  | 0.000042 (n = 1) |
| SR039 | 4-fluoro |  | 0.000085 ± 0.00007 |
|  | 5-fluoro[c] | 0.0045 ± 0.003 | 0[a] |
| SR043 | 6-fluoro |  | 0.00995 (n = 2) |
| SR022 | 7-fluoro (90% pure) | 0.053 ± 0.022 | 0[a] |

Figure 2:
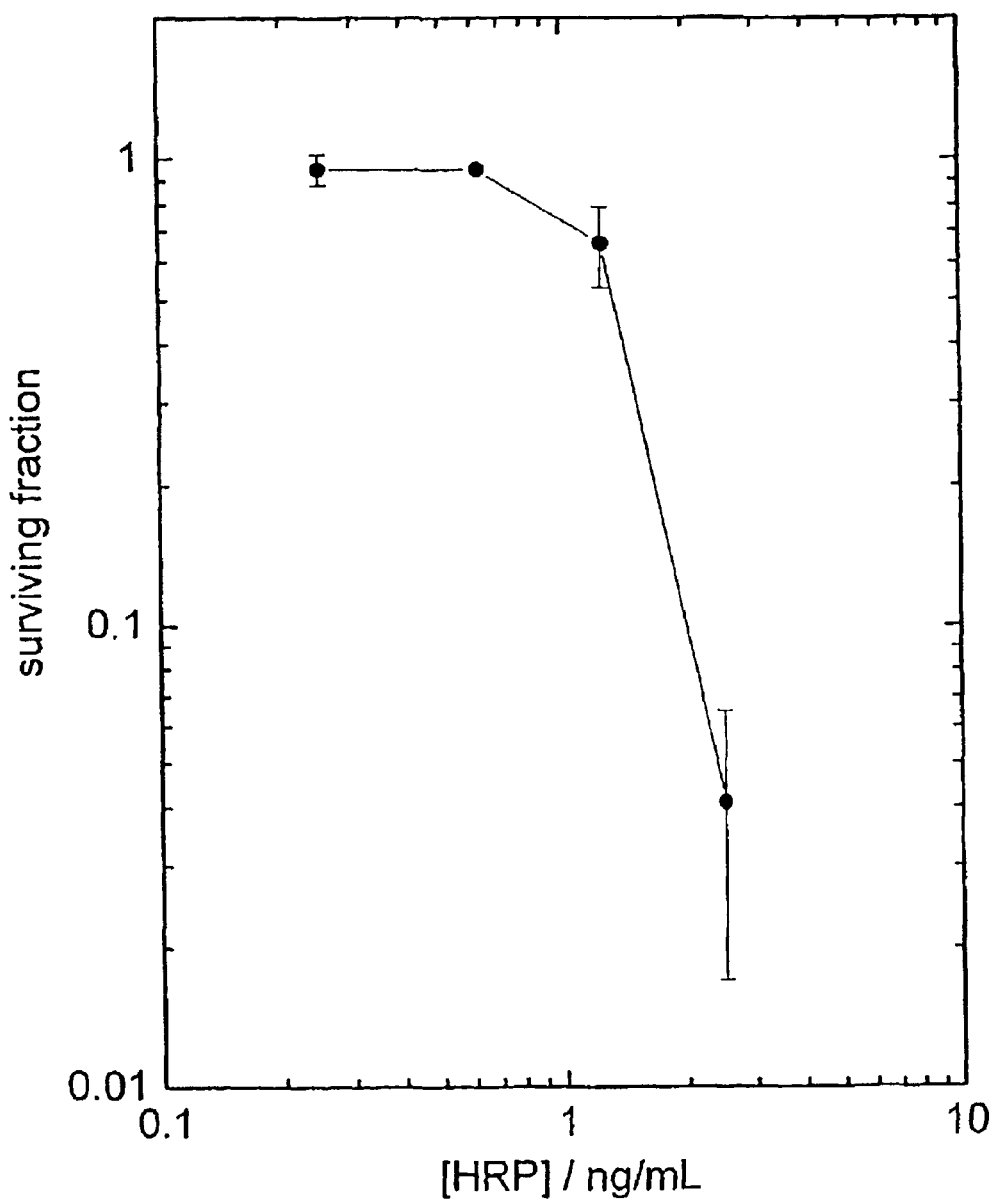
FIG. 2 shows the variation in the surviving fraction of V79 cells against the varying concentration of HRP, following 5 hours incubation, with 50 µM of the same compound of formula (I) as in FIG. 1, 5-fluoro-indole-3-acetic acid.

*= comparative example
[a]= all cells killed
[b]= no detectable effect
[c]= commercially available FIGS. 1 and 2 relate to experiments carried out using 5-fluoro-indole-3-acetic acid. FIG. 1 shows the variation in the surviving fraction of cells against varying concentration of 5-fluoro-indole-3-acetic acid, following 5 hours incubation, with or without HRP (1.2 μg/L). FIG. 2 shows the variation in the surviving fraction of cells against the varying concentration of HRP, following 5 hours incubation, with 50 μM of 5-fluoro-indole-3-acetic acid.

Example 7(b)

Human Cell Lines

Human breast carcinoma cells (MCF7) and human colon carcinoma cells (HT29) were obtained from the European Tissue Culture Collection. Cells were grown as attached monolayers in EMEM supplemented with 10% foetal calf serum, 2 mM L-glutamine, 5% w/v non-essential amino acids, 100 U/mL penicillin and 100 µg/mL streptomycin, and incubated in a humidified incubator at 37° C., in 5% $CO_2$/air. Cell survival experiments were carried out exactly as for V79 cells except that cells were plated into Petri dishes directly from a trypsinised confluent flat and allowed to plate for at least 4 hours before addition of the drug.

Figure 3:
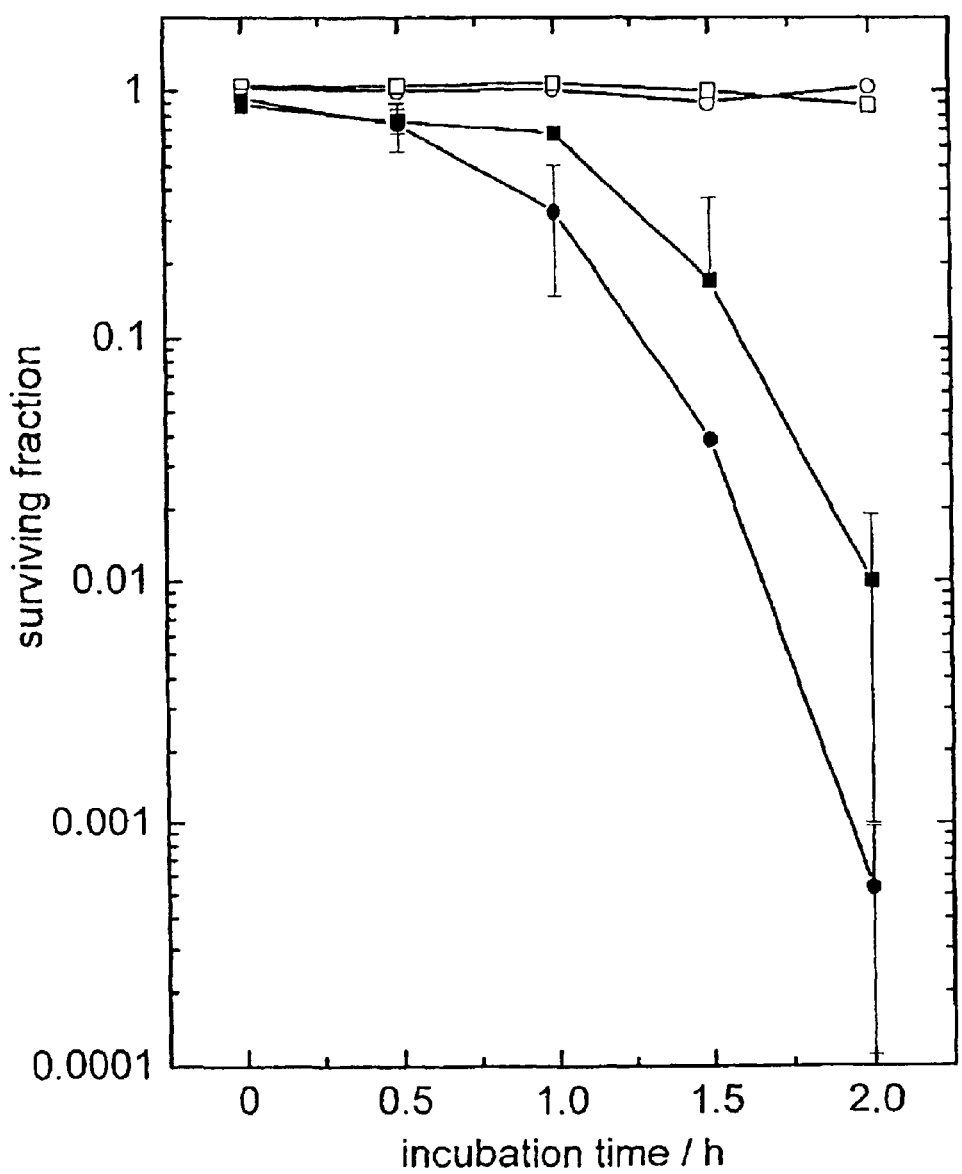
FIG. 3 shows the variation in the surviving fraction of MCF7 and HT29 cells when incubated for varying lengths of time with 100 µM of the same compound of formula (I) as in FIGS. 1 and 2, 5-fluoro-indole-3-acetic acid and with or without HRP (1.2 µg/L).

FIG. 3 shows the variation in the surviving fraction of MCF7 and HT29 cells when incubated for varying lengths of time with 100 µM 5-fluoro-indole-3-acetic acid and with or without HRP (1.2 µg/L).

Example 8

Measurements of the Cytotoxic Effects of Treatment with Compounds of Formula (I) and Horseradish Peroxidase (HRP) Bound to a Polymer (Polymer Directed Enzyme-Prodrug Therapy, PDEPT)

Preparation of the HRP-Polymer Conjugate

HRP was conjugated to polyethylene glycol (PEG) based on the method of Fortier and Laliberté (1993, ibid.). HRP (7.82 mg) was mixed with methoxypoly(ethylene glycol)-nitrophenyl carbonate (PEG, Shearwater Polymers, Huntsville, Ala., USA) molecular weight 5240 Da (42.66 mg) in 4 mL 0.1 M borate buffer pH 9.4 overnight at 4° C. The following day 50 mL 35 mM sodium phosphate buffer pH 6.5 was added and the resulting yellow p-nitrophenol removed by filtering through a Vectraspin (Whatman) 20 kDa cut off filter. The resulting concentrated mixture of HRP and HRP-PEG conjugate was stored overnight in a refrigerator. The proteins were separated on a Sephadex G 75 superfine column (2×35 cm) with 25 mM sodium acetate pH 5 at 1 mL/h, 4° C. and 1 hour fractions collected with a fraction collector. HRP was measured spectrophotometrically at 405 nm. The purity of the fractions was measured on a SDS-PAGE gel (8% agarose gel with 4% stacking gel) and the bands stained with Coomassie Blue (0.25 g Coomassie Blue in 10 mL glacial acetic acid and 90 mL 50% methanol) for 50 minutes. The gel was destained overnight with 10 mL glacial acetic acid and 90 mL 50% methanol. Approximately 10 mg pure HRP-PEG conjugate was obtained with a range of molecular weights up to 25 kDa greater than pure HRP. The resulting protein was dried under nitrogen and stored under nitrogen at −20° C.

Measurement of the Peroxidase Activity of the HRP-Polymer. Conjugate

Activity of the HRP-PEG was measured using the Sigma ABTS (2,2'-azino-bis(3-ethylbenzthiazoline-6-sulfonic acid) method. ABTS (0.725 mL of 9.1 mM in 0.1M potassium phosphate buffer pH 5), 12.5 µM HRP solution (approximately 20 µg/ml in 40 mM phosphate buffer with 0.25% bovine serum albumin and 0.5% w/v Triton X-100 pH 6.8), and 25 µL 0.3% hydrogen peroxide were mixed, and the rate of increase in absorbance at 406 nm measured (with a 400 nm cut off filter) on a Hewlett Packard 8452A diode array spectrophotometer. Assuming an extinction coefficient of 36,800 $M^{-1}$ $s^{-1}$, the activity of HRP/PEG was calculated from the unit definition: 1 unit HRP will oxidise 1 µmol of ABTS per minute at pH 5, 25° C.

Biodistribution Studies of the HRP-Polymer Conjugate

Experiments to measure tissue uptake of HRP-PEG were carried out in female CBA/Gy mice with a subcutaneous dorsum breast adenocarcinoma tumour (CaNT). Tumours arose from inoculation with a 0.5 mL suspension of a disaggregated solid tumour under an inhalation anaesthetic. Tumours were used approximately 3 weeks later (the tumours had an average mass of about 0.4 g).

Mice were injected intra-peritoneally (i.p.) with 0.3 mL 0.5 mg/mL HRP-PEG, intra-tumour (i.t.) with 50 µL 3 mg/mL HRP-PEG or intra-venously (i.v.) with 100 µL 1.5 mg/mL HRP-PEG. The mice were killed by cervical dislocation up to 48 hours later, the tissues removed, weighed and stored at −20° C. Blood was removed from the chest cavity, spun down and the plasma stored at −20° C.

HRP-PEG tissue accumulation was measured using tetramethylbenzidine (TMB). Tissues were macerated in 2 mL 0.5% hexadecyltrimethyl ammonium bromide in 50 mM phosphate buffer (pH 6) and freeze-thawed twice. The suspensions were heated at 60° C. for 2 h, centrifuged at 4500 rpm for 5 mins, and stored at −20° C. Enzyme activity was measured by mixing 1.87 mL 80 mM phosphate buffer pH 5.4, 70 µL 88 mM hydrogen peroxide, 20 µL 1 mg/mL TMB in 10% dimethyl sulphoxide (DMSO) and 40 µl sample. The rate of increase in absorbance at 630 nm was measured with a Hewlett Packard 8452A diode array spectrophotometer. The absorbance change per minute was calculated relative to protein content of the samples which were measured by a Bio Rad Lowry method after being diluted 10-fold in water. Enzyme levels were measured relative to control levels which allowed inaccuracies from variations in haemoglobin content to be eliminated. Uptake of HRP-PEG into the tumour occurred after i.p. and i.t. injection although liver uptake was high. Injection of HRP-PEG i.t. allowed activity to be measured in the tumour up to 20 hours later. Without wishing to be bound by theory, liver uptake is thought to be due to mannose glycoprotein receptors on hepatocyte cells selectively taking up HRP (which is a mannose glycoprotein) from the circulation, which may be avoided by protein modification without affecting the activity (J W Tams, K G Welinder, Anal. Biochem. 1995, 228, 48–55).

Example 9

Measurements of the Cytotoxic Effects of Treatment with Compounds of Formula (I) and Horseradish Peroxidase (HRP) Bound to an Antibody (Antibody Directed Enzyme-Prodrug Therapy, ADEPT)

The Tumour Xenograft Used

The human colon adenocarcinoma cell line LS174T was used to develop a xenograft model in the flanks of MF1 nude mice. Subsequent passaging was by subcutaneous implantation of small tumour pieces (approximately 1 $mm^3$). The tumour is a poor- to moderately-differentiated carcinoembryonic antigen-(CEA)-producing adenocarcinoma with small glandular acini, which secretes no measurable CEA into the circulation. All mice used were females aged 2–3 months and weighing 20–25 g.

The Antibody Used

The A5B7 antibody was used. This is a monoclonal anti-CEA antibody, which gives positive staining for glandular luminal surface and cytoplasm in the LS174T xenograft model. The antibody was labelled with $^{125}I$ using the iodogen method, to a specific activity of 37 MBq/1 mg protein, and sterilised by passing through a 0.22 mm filter (Gelman, Northampton, UK).

Preparation of the Antibody-Enzyme Conjugate

The method of Nakane and Kawaoi (1974) as modified by Hudson and Hay (1980) was used. The A5B7 antibody was dialysed three times against 0.2 M sodium carbonate buffer pH 9.5 at 4° C. HRP (Sigma Type VI, RZ~3.0, 4 mg) was dissolved in 1.0 ml deionized water. Freshly prepared sodium periodate (200 μL, 0.1 M) was added to the mixture and stirred gently for 20 minutes at room temperature to activate the HRP. The solution was dialysed overnight against sodium acetate (1 L, 1 mM pH 4.4) at 4° C. Carbonate buffer (20 μL, 0.2 M) was added to the dialysed HRP aldehyde, raising the pH to 9–9.5 just before addition of the antibody to be labelled. The solution was incubated at room temperature for 2 hours with gentle stirring. Sodium borohydride (100 μL 4 mg/ml freshly prepared) was added and left for 2 hours at 4° C. to reduce the free enzyme. The solution was then dialysed overnight against borate buffer (2 L 0.1 M pH 7.4). The labelled antibodies were stored at 4° C.

Studies of the Biodistribution of the Antibody-Enzyme Conjugate

The conjugate labelled with $^{125}$I was used in some experiments. Using groups of 4 mice, antibody and antibody-enzyme distribution was investigated at 6, 24 and 48 hours after antibody injection. All mice received 0.75 MBq/20 g $^{125}$I-A5B7 i.v. into the tail vein. At the selected time points the mice were bled, and liver, kidney, lung, spleen, colon, muscle and tumour removed for comparative activity assessment. Each tissue was weighed, digesting in 7 M KOH, and counted by gamma counter (Wizard: Pharmacia, Milton Keynes, UK). Results were expressed as percentage injected dose per g tissue, and the groups compared using the Mann-Witney U test. Mice were given food and water ad libitum, the water containing 0.1% potassium iodide to block thyroid uptake of iodine.

In other experiments the enzyme activity of the HRP-A5B7 conjugate was measured. Using two groups of four LS174T tumour-bearing nude mice, antibody-enzyme activity and distribution was measured in tissues 24 and 72 hours after antibody injection. All mice were injected i.v. with 250 μg HRP-A5B7 into the tail vein. Mice were bled at the selected time points and the tumour, liver, lung, kidney, muscle and plasma removed and stored at −20° C. Enzyme activity was measured using the tetramethyl benzidine method described above for assay of the HRP-PEG conjugate. Activity was measured relative to untreated control tumour-bearing mice.

Example 10

Measurements of the Cytotoxic Effects of Treatment with Compounds of Formula (I) Combined with Photosensitizers and Visible Light in Photodynamic Therapy (PDT)

V79 hamster cells were photolysed in the presence of a variety of photosensitizers and compounds of formula (I).

V79 cells were plated for at least 1 hours in EMEM on 6-well plates in duplicate in phenol free DMEM. The medium was removed from the cells in the dark and 2 mL 2 μM of the photosensitzer and 0.1 mM of the test compound (5-fluoro IAA and 5-bromo IAA) added in the dark and immediately photolysed for varying lengths of time using a matrix of light-emitting diodes at the appropriate wavelength for the photosensitizer. The cells were left in an incubator for 1 hour, the drugs removed, the cells washed with 2 mL PBS solution in the dark and then left to grow for 6 days in 3 mL EMEM. Colonies of >50 cells were counted after fixing and staining with crystal violet (see above).

The results in terms of surviving fraction of cells (relative to untreated control cells) against increasing photolysis time are shown in the figures indicated below.

| Photo-sensitizer | Methylene Blue | Thionine | Toluidine Blue | Rose Bengal |
|---|---|---|---|---|
| Wavelength of irradiating light (nm) | 660 | 630 | 630 | 574 |
| Figure for results | 4a | 4b | 4c | 4d |

Very little toxicity was seen with the photosensitizer or IAA alone at the same concentrations. Toxicity may be due to the formation of the putative cytotoxins, 3-methylene-2-oxindoles which were shown to be formed by high performance liquid chromatography.

Example 11

Measurements of the Cytotoxic Effects of Treatment with Compounds of Formula (I) and Horseradish Peroxidase (HRP) Using Cells Transiently Transfected with the HRP Encoding Gene (Gene Directed Enzyme-Prodrug Therapy, GDEPT)

Human bladder carcinoma T24 cells, MCF-7 mammary carcinoma cells (both from European Collection of Cell Cultures, Salisbury, UK), FaDu, nasopharyngeal squamous carcinoma cells (American Type Culture Collection, Manassas, Va.) were maintained in Dulbecco's modified Eagle's medium (DMEM) supplemented with 10% foetal calf serum, 2 mM L-glutamine, 100 U/ml penicillin, 100 g/ml streptomycin, and incubated in a humidified incubator at 37° C. and 5% $CO_2$/air. Only cells which tested negative for mycoplasma infection were utilised.

The plasmid pRK34-HRP containing the HRP cDNA was provided by Dr D F Cutler, University College, London (Connolly CN, Futter CE, Gibson A, et al., Transport into and out of the Golgi complex studied by transfecting cells with cDNAs encoding horseradish peroxidase. J. Cell Biol. 1994; 127: 641–652).

Transient transfectants were obtained by exposing the cells to complexes of integrin-targeted peptides, lipofectin and DNA (Hart SL, Arancibia-Cárcamo CV, Wolfert MA, et al. Lipid-mediated enhancement of transfection by a nonviral integrin-targeting vector. Human Gene Ther. 1998; 9: 575–585) and were assayed for gene expression after 24 h. Transfection efficiency was estimated at about 20% for T24 cells, 16–20% for MCF-7 cells and 10–14% for FaDu cells.

Exponential growing transfected and untransfected cells were counted and plated at low density on Petri dishes and exposed to compounds of formula (I) for 24 hours in phenol-red-free Hanks' balanced salt solution (HBSS) in a 37° C. incubator.

Alternatively, to test activity in hypoxic conditions, T24 cells were pre-plated in an anaerobic cabinet and, after incubation for 5 to 6 hours to ensure anoxic conditions, were exposed to compounds of formula (I) for 24 hours in the cabinet. All plastics and media were pre-incubated in anoxia for 48 hours before use to remove residual oxygen.

Following drug exposure, cells were rinsed with PBS and grown for 8 to 20 days in complete DMEM supplemented with feeder cells (V79 cells exposed to 250 Gy $^{60}$Co irradiation). After fixation and staining with 2.5% crystal violet w/v in methylated spirit, colonies of >50 cells were scored. Surviving fractions were evaluated relative to HBSS-treated controls.

Figure 5:
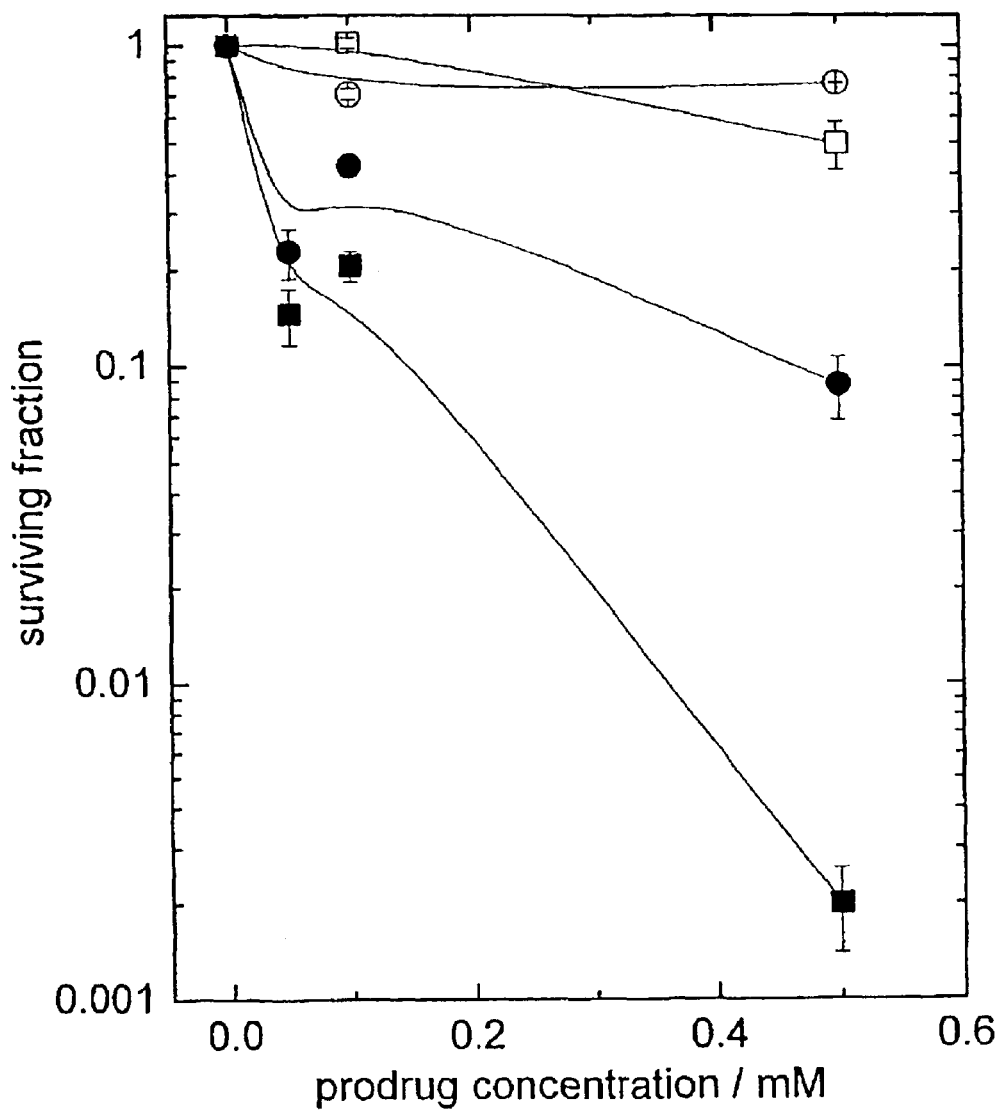
FIG. 5 shows the variation in the surviving fraction of transfected and control T24 cells after 24 hours incubation against varying concentrations of compounds of formula (I), 5-fluoro-indole-3-acetic acid or 5-bromo-indole-3-acetic acid.

FIG. 5 shows the variation in the surviving fraction of transfected and control T24 cells in oxic conditions against varying concentrations of 5-fluoro-indole-3-acetic acid or 5-bromo-indole-3-acetic acid.

A concentration of test compound to reduce cell survival by 50% ($IC_{50}$) was estimated from the survival curves, and are tabulated below, where $HRP^+$ represents transfected cells, $HRP^-$ untransfected cells, and factor the ratio of $IC_{50}$ for transfected cells to untransfected cells.

|     | T24 (normoxic) | | | MCF-7 | | | FaDu | | | T24 (anoxic) | | |
| --- | --- | --- | --- | --- | --- | --- | --- | --- | --- | --- | --- | --- |
|     | $HRP^+$ | $HRP^-$ | factor | $HRP^+$ | $HRP^-$ | factor | $HRP^+$ | $HRP^-$ | Factor | $HRP^+$ | $HRP^-$ | factor |
| 5F  | 0.04 | 3.5 | 88 | 0.25 | 0.4 | 1.6 | 0.02 | 1.2 | 60 | 0.03 | 2.3 | 77 |
| 5Br | 0.006 | 0.6 | 100 | 0.007 | 0.5 | 71 | 0.007 | 0.6 | 86 | 0.007 | 1 | 43 |

Example 12

Distribution of 5-fluoro-indole Acetic Acid in vivo in Mice with the Carcinoma NT Tumour 5-fluoro-indole acetic acid (5 mg/mL) in 2% v/v ethanol/water was adjusted to pH 7.4 with NaOH and injected i.p. at a dose of 50 mg/kg into female CBA mice bearing the Carcinoma NT tumour (see example 8 for details). The mice were sacrificed up to 2 hours after drug administration and the blood and tissues removed immediately and placed on ice. The whole blood was spun down and the plasma stored at −20° C. Tissue sample were weighed and homogenised in 4 to 9 volumes of ice-cold water. The homogenised tissue was then stored at −20° C.

For HPLC analysis, plasma (50 μL) was mixed with IAA internal standard (130 μM, 25 μL) and protein precipitated with acetonitrile (50 μL). The samples were spun down and the supernatant injected directly for HPLC analysis. For tissue levels, samples (250 μL) was mixed with IAA internal standard (130 μM, 25 μL) and precipitated with acetonitrile (250 μL) for direct injection for HPLC analysis. HPLC analysis was carried out with a Hypersil SODS 125×4.6 mm column eluting with A; 75% acetonitrile and B: 20 mM ammonium acetate (pH 5.1) with a gradient of 15–70% A in 10 minutes at 2 mL/minute. Detection was at 290 nm using a Waters 486 variable wavelength detector.

Figure 6:
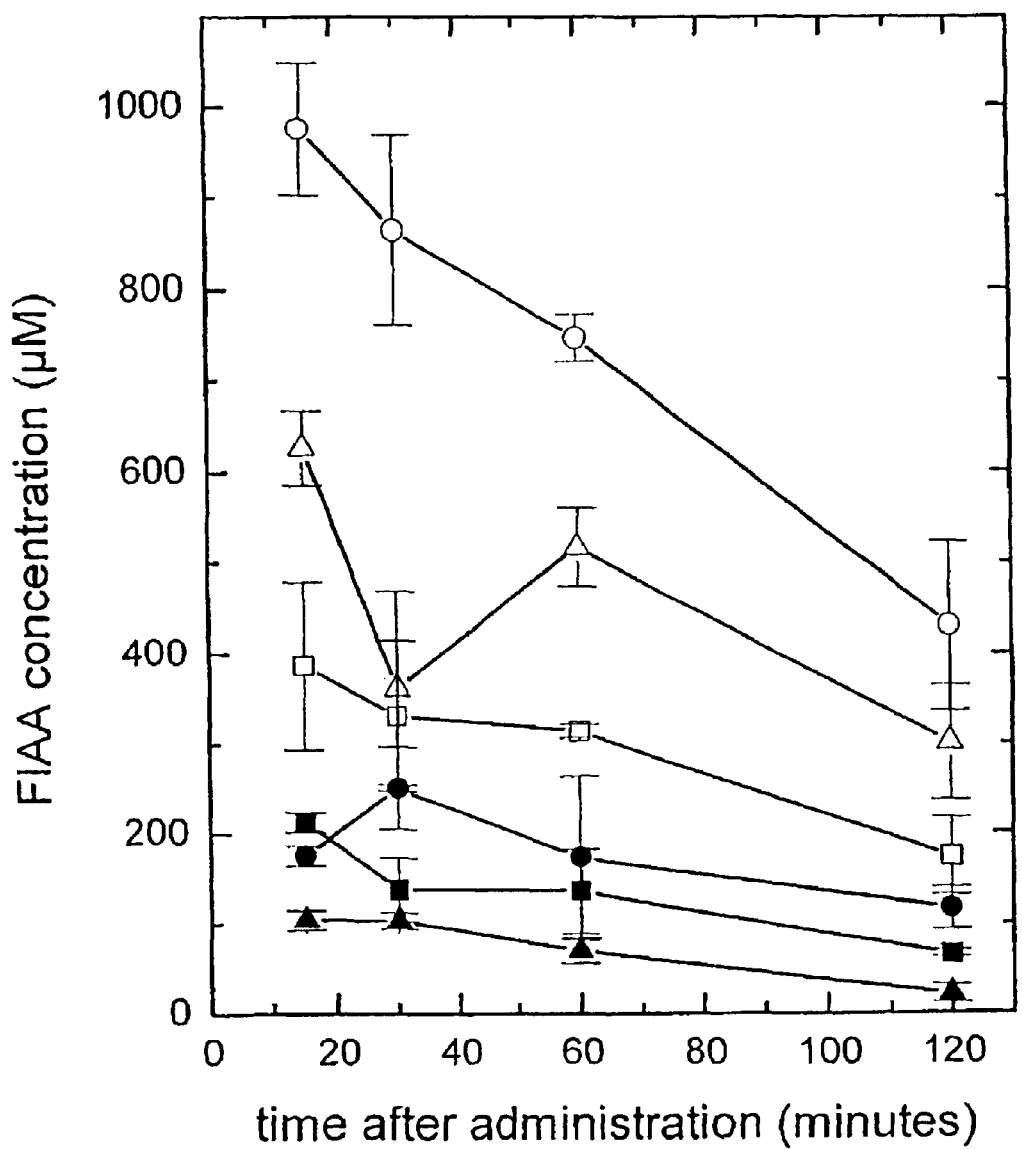
FIG. 6 shows the variation in concentration of 5-fluoro-indole-3-acetic acid in plasma and tissues following intraperitoneal injection into mice.

The amount of 5-fluoro-indole acetic acid in the samples is illustrated in FIG. 6. These results show that sufficient concentrations to achieve a cytotoxic effect are attained in the tumour. High levels in the kidney are consistent with excretion of substantial amounts of the compound unchanged, which, without wishing to be bound by theory, results from the blocking of hydroxylation by P450s by the 5 fluorine substituent.

FIGURE LEGENDS

Figure 4A:
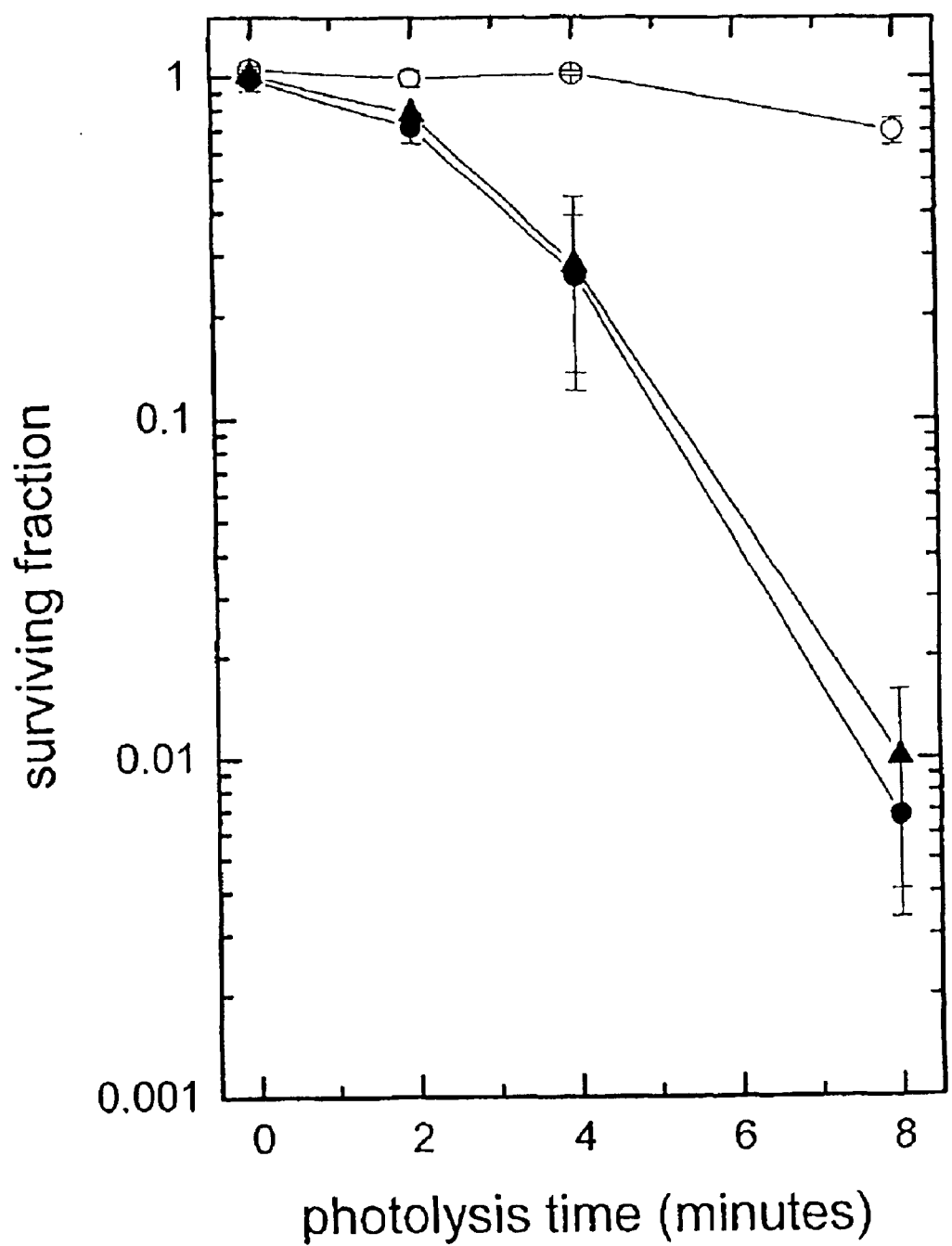
FIG. 4a shows the variation in the surviving fraction of V79 cells following 1 hour incubation against varying photolysis time of the cells in conjunction with methylene blue, optionally in the presence of compounds of formula (I), 5-fluoro-indole-3-acetic acid or 5-bromo-indole-3-acetic acid.
Figure 4B:
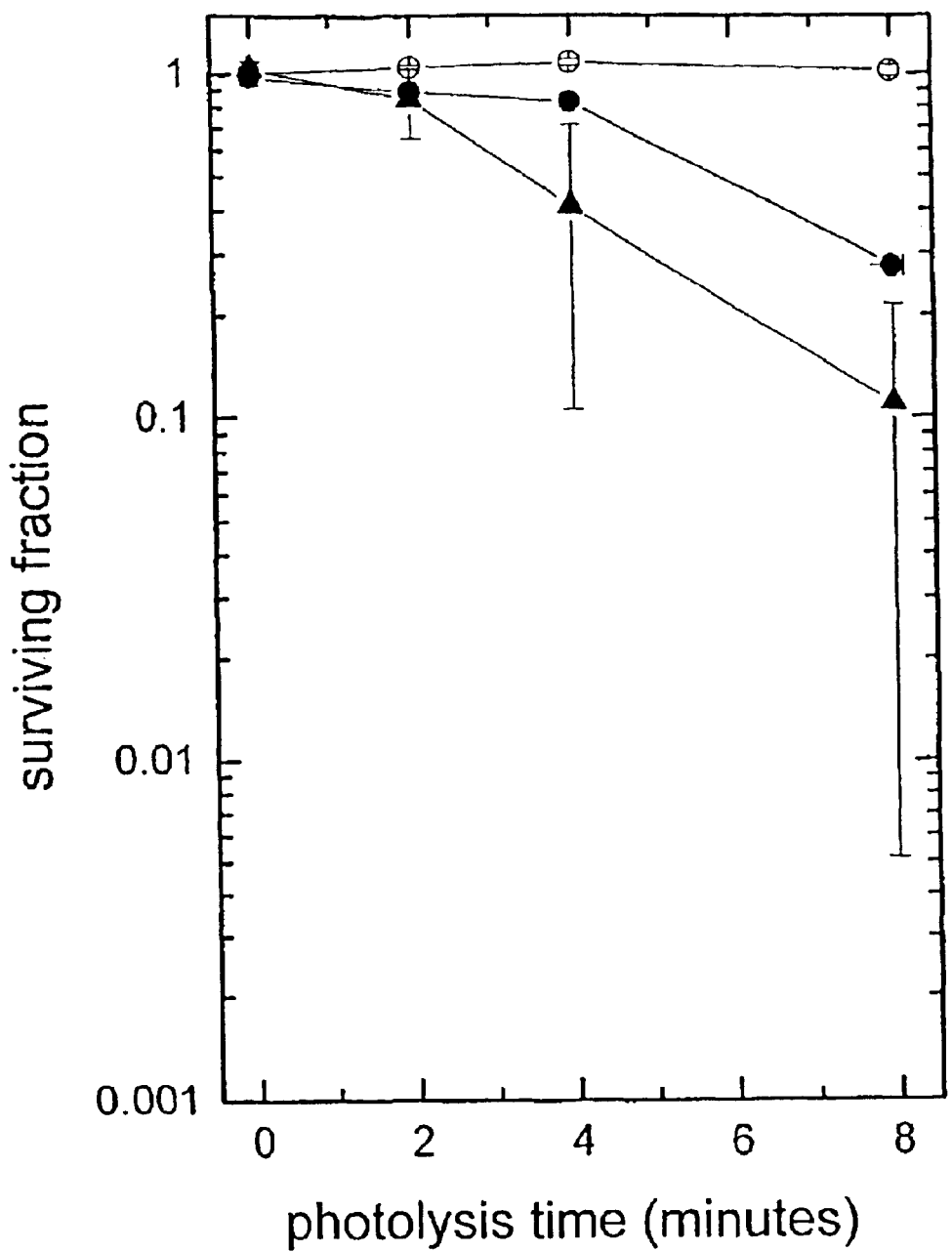
FIG. 4b is similar to FIG. 4a, except that thionine was used in place of methylene blue.
Figure 4C:
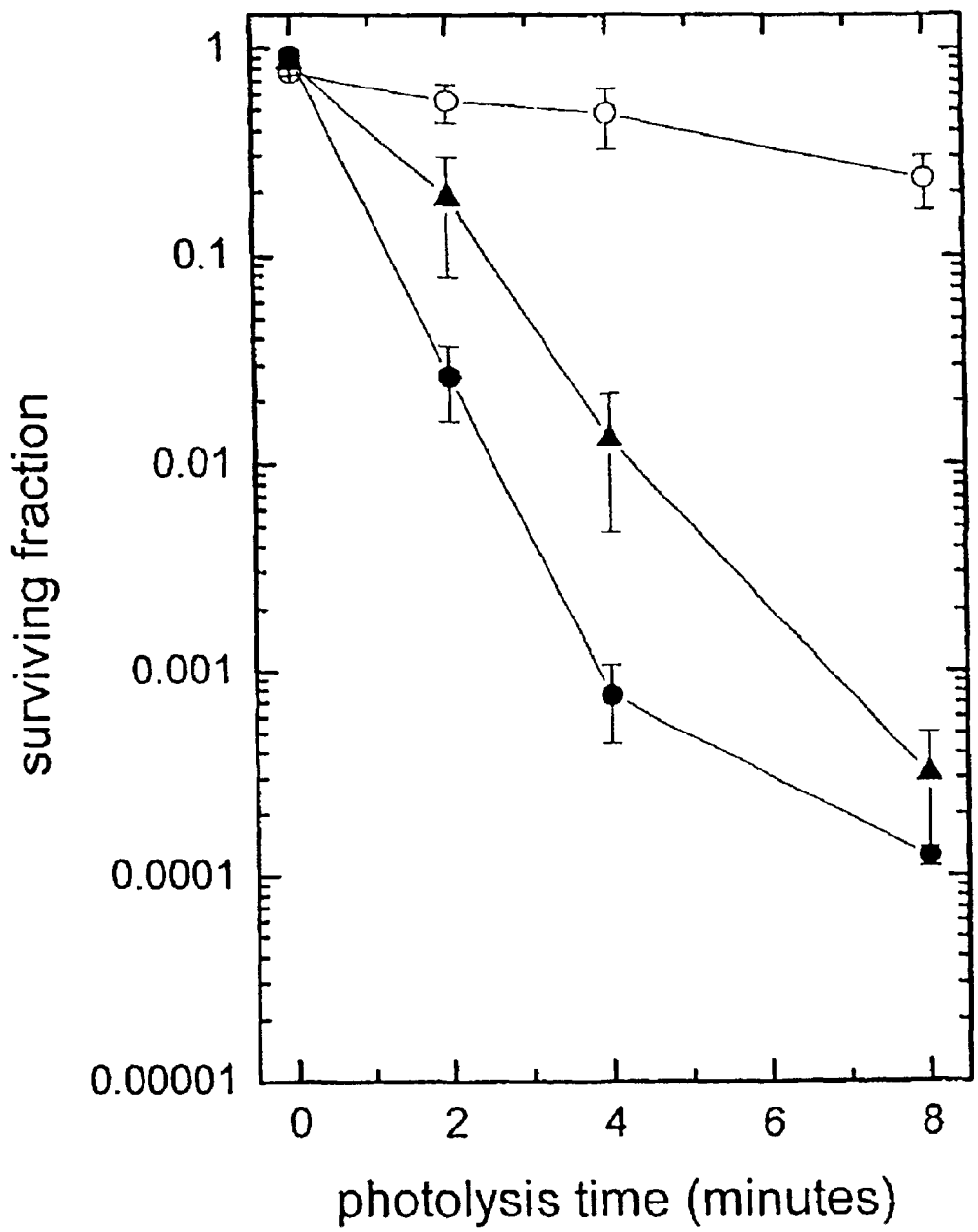
FIG. 4c is similar to FIG. 4a, except that toluidine blue was used in place of methylene blue.
Figure 4D:
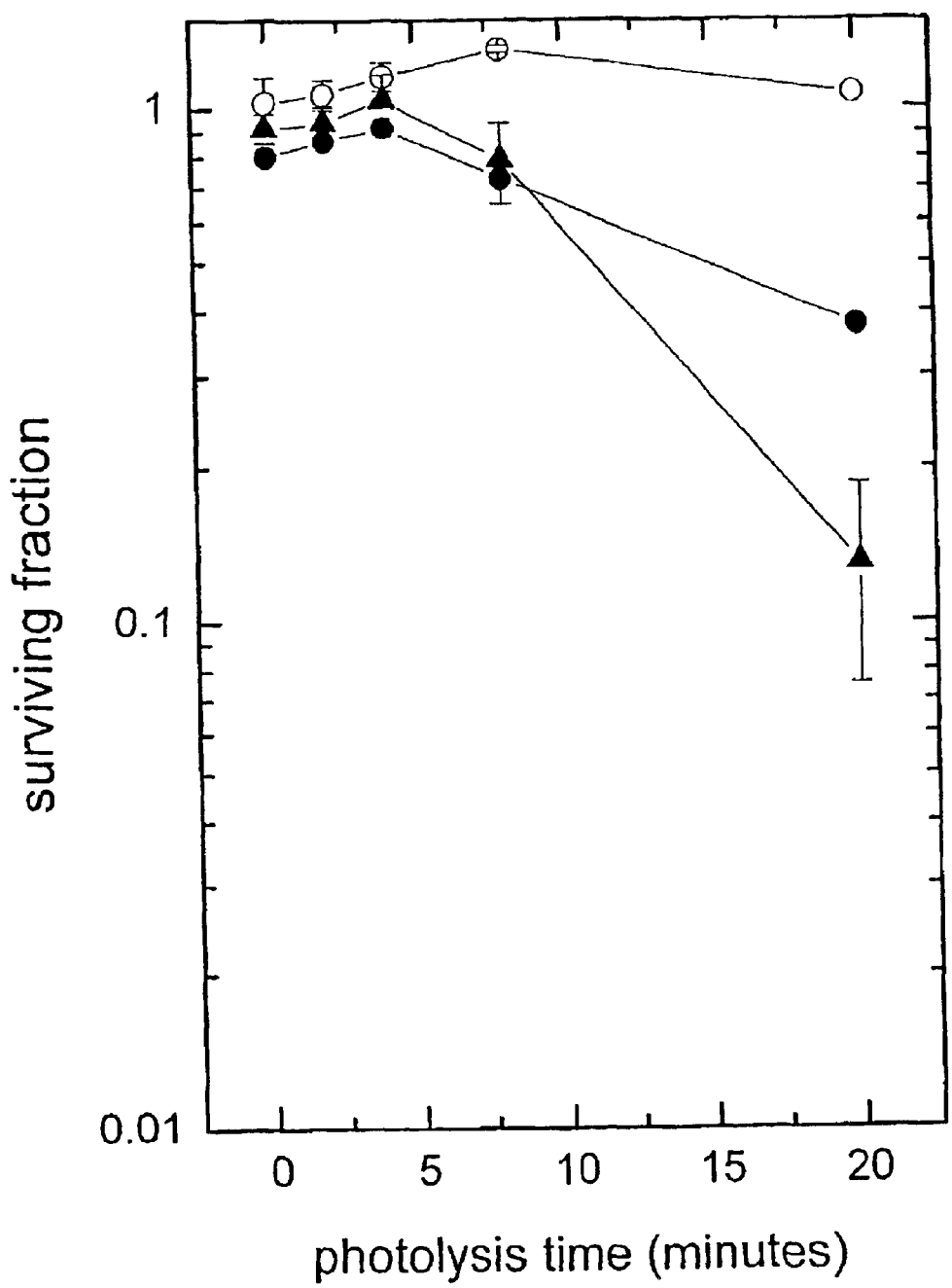
FIG. 4d is similar to FIG. 4a, except that rose bengal was used in place of methylene blue.

FIG. 1: -●- with HRP; -o- Without HRP
FIG. 3: -o- MCF7 controls; -●- MCF7+5-F-IAA/HRP; -□- HT29 controls; -■- HT29+5-F-IAA/HRP
FIG. 4a: -o- methylene blue alone
-●- methylene blue+5-F-IAA
-▲- methylene blue+5-Br-IAA
FIG. 4b: -o- thionine alone
-●- thionine+5-F-IAA
-▲- thionine blue+5-Br-IAA FIG. 4c: -o- toluidine blue alone
-●- toluidine blue+5-F-IAA
-▲- toluidine blue+5-Br-IAA
FIG. 4d: -o- rose bengal alone
-●- rose bengal+5-F-IAA
-▲- rose bengal+5-Br-IAA
FIG. 5: -o- control+5-F-IAA;
-●- transfectants+5-F-IAA;
-□- control+5-Br-IAA;
-■- transfectants+5-Br-IAA
FIG. 6: -o- plasma
-●- tumour
-□- liver
-■- heart
-Δ- kidney
-▲- muscle

What is claimed is:

1. A pharmaceutical composition comprising a compound, of formula (I):

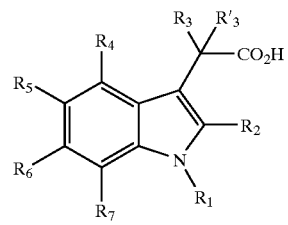

and a pharmaceutically acceptable carrier or diluent; wherein $R_2$ is H;

$R_1$, $R_3$ and $R'_3$ are independently selected form H or lower alkyl;

$R_4$, $R_5$, $R_6$ and $R_7$ are independently selected from H, electron withdrawing groups, lower alkyl groups, lower alkoxy groups, aryl groups or aryloxy groups, wherein at least one of $R_4$, $R_5$, $R_6$ and $R_7$ is selected from an electron withdrawing group.

2. The pharmaceutical composition according to claim 1, wherein the electron withdrawing group is selected from the group consisting of F, Cl, Br, 1, $OCF_3$, carboxyl, acetal and electron deficient aryl.

3. The pharmaceutical composition according to claim 2, wherein the electron withdrawing group is selected from the group consisting of F, Ca, Br and I.

4. The pharmaceutical composition according to claim 1, wherein the balance of the substituents $R_4$, $R_5$, $R_6$ and $R_7$ is electron withdrawing.

5. The pharmaceutical composition according to claim 1, wherein $R_1$ is independently selected from H or optionally substituted saturated lower alkyl groups.

6. The pharmaceutical composition according to claim 5, wherein $R_1$ is independently selected from H, methyl or ethyl.

7. The Pharmaceutical composition according to claim 1, wherein $R'_3$ is H.

8. The pharmaceutical composition according to claim 1, wherein $R_3$ is selected from H or optionally substituted saturated lower alkyl groups.

9. The pharmaceutical composition according to claim 8, wherein $R_3$, is selected from H, methyl or ethyl.

10. The pharmaceutical composition according to claim 1, wherein one or two of $R_4$, $R_5$, $R_6$, and $R_7$, are independently selected from electron withdrawing groups.

11. The pharmaceutical composition according to claim 1, wherein if one or more of $R_4$, $R_5$, $R_6$, and $R_7$, are not H or an electron withdrawing groups, they am selected from optionally substituted saturated lower alkyl groups.

12. The pharmaceutical composition according to claim 11, wherein those of $R_4$, $R_5$, $R_6$, and $R_7$, which are not H or an electron withdrawing group are selected from H, methyl or ethyl.

13. The pharmaceutical composition according to claim 1, wherein one of $R_4$, $R_5$, $R_6$ and $R_7$, is an electron withdrawing group and the rest are H.

14. The pharmaceutical composition according to claim 1, wherein the balance of the substituents $R_4$, $R_6$ and $R_7$, is electron withdrawing.

\* \* \* \* \*